United States Patent
Ow et al.

(10) Patent No.: US 12,228,512 B2
(45) Date of Patent: Feb. 18, 2025

(54) MULTIPURPOSE MICROFLUIDICS DEVICES FOR RAPID ON-SITE OPTICAL CHEMICAL ANALYSIS

(71) Applicant: Saudi Arabian Oil Company, Dhahran (SA)

(72) Inventors: Hooisweng Ow, Woburn, MA (US); Sehoon Chang, Brighton, MA (US); Jason R. Cox, Ashland, MA (US); Bora Yoon, Houston, TX (US); Wei Wang, Quincy, MA (US)

(73) Assignee: Saudi Arabian Oil Company, Dhahran (SA)

( * ) Notice: Subject to any disclaimer, the term of this patent is extended or adjusted under 35 U.S.C. 154(b) by 648 days.

(21) Appl. No.: 16/931,143

(22) Filed: Jul. 16, 2020

(65) Prior Publication Data

US 2021/0018436 A1  Jan. 21, 2021

Related U.S. Application Data

(60) Provisional application No. 62/874,652, filed on Jul. 16, 2019.

(51) Int. Cl.
 G01N 21/64 (2006.01)
 B01L 3/00 (2006.01)
 (Continued)

(52) U.S. Cl.
 CPC .... G01N 21/6408 (2013.01); B01L 3/502715 (2013.01); G01N 1/405 (2013.01);
 (Continued)

(58) Field of Classification Search
 CPC .............. G01N 21/6408; G01N 1/405; G01N 33/2823; B01L 3/502715; B01L 2300/126; B01L 2300/161
 See application file for complete search history.

(56) References Cited

U.S. PATENT DOCUMENTS

| | | | |
|---|---|---|---|
| 3,703,355 A | 11/1972 | Takahashi | |
| 3,851,171 A | 11/1974 | Saniford | |

(Continued)

FOREIGN PATENT DOCUMENTS

| | | |
|---|---|---|
| CA | 2997608 | 4/2017 |
| CN | 101475667 | 7/2009 |

(Continued)

OTHER PUBLICATIONS

General Electric, "Laboratory filtration-Product guide" (Year: 2018).*

(Continued)

*Primary Examiner* — Brian J. Sines
(74) *Attorney, Agent, or Firm* — Fish & Richardson P.C.

(57) ABSTRACT

Devices for chemical analysis include a first separation element formed on the substrate, the first separation element having a wicking surface that separates water from hydrocarbons in a fluid sample, a hydrophobic barrier at least partially surrounding the first separation element, a second separation element fluidically connected the first separation element, the second separation element configured to trap salts and organic matter present in the fluid sample, and a detection element fluidically connected to the second separation element, the detection element having a surface that binds with one or more analytes that may be present in the fluid sample and thereby emits a signal that is capable of being optically detected by a detector. Methods include providing such a device for chemical analysis, placing the fluid sample on the first separation element, and detecting the signal emitted by the detection element.

24 Claims, 17 Drawing Sheets

(51) Int. Cl.
  *G01N 1/40* (2006.01)
  *G01N 33/28* (2006.01)
(52) U.S. Cl.
  CPC .... *G01N 33/2823* (2013.01); *B01L 2300/126* (2013.01); *B01L 2300/161* (2013.01)

(56) References Cited

U.S. PATENT DOCUMENTS

| | | |
|---|---|---|
| 3,947,396 A | 3/1976 | Kangas et al. |
| 4,137,452 A | 1/1979 | Paap |
| 4,264,329 A | 4/1981 | Beckett |
| 4,289,203 A | 9/1981 | Swanson |
| 4,420,565 A | 12/1983 | Schmitt |
| 4,694,046 A | 9/1987 | Bock et al. |
| 4,755,469 A | 7/1988 | Showalter |
| 4,772,563 A | 9/1988 | Evangelista et al. |
| 4,882,763 A | 11/1989 | Buchan et al. |
| 5,124,268 A | 6/1992 | Dakubu |
| 5,168,927 A | 12/1992 | Stegenneier |
| 5,990,224 A | 11/1999 | Raynolds et al. |
| 6,226,390 B1 | 5/2001 | Deruyter et al. |
| 6,250,848 B1 | 6/2001 | Moridis et al. |
| 6,252,016 B1 | 6/2001 | Wu et al. |
| 6,331,436 B1 | 12/2001 | Richardson |
| 6,488,872 B1 | 12/2002 | Beebe et al. |
| 6,585,044 B2 | 7/2003 | Rester |
| 6,590,647 B2 | 7/2003 | Stephenson |
| 6,691,780 B2 | 2/2004 | Nguyen et al. |
| 7,032,662 B2 | 4/2006 | Malone |
| 7,033,975 B2 | 4/2006 | Baran, Jr. et al. |
| 7,249,009 B2 | 7/2007 | Ferworn et al. |
| 7,289,942 B2 | 10/2007 | Yang et al. |
| 7,303,006 B2 | 12/2007 | Stone |
| 7,373,073 B2 | 5/2008 | Kamp et al. |
| 7,472,748 B2 | 1/2009 | Gdanski et al. |
| 7,520,933 B2 | 4/2009 | Park et al. |
| 7,526,953 B2 | 5/2009 | Goodwin et al. |
| 7,588,827 B2 | 9/2009 | Nie et al. |
| 7,810,563 B2 | 10/2010 | Buijse et al. |
| 7,875,654 B2 | 1/2011 | Hong et al. |
| 7,879,625 B1 | 2/2011 | Boss |
| 7,920,970 B2 | 4/2011 | Zuo et al. |
| 8,028,562 B2 | 10/2011 | Shah et al. |
| 8,062,418 B2 | 11/2011 | Costantz et al. |
| 8,148,477 B2 | 4/2012 | Saita et al. |
| 8,176,981 B2 | 5/2012 | Savu et al. |
| 8,187,554 B2 | 5/2012 | Panagiotou |
| 8,269,501 B2 | 9/2012 | Schmidt et al. |
| 8,337,783 B2 | 12/2012 | Locascio et al. |
| 8,418,759 B2 | 4/2013 | Moore et al. |
| 8,627,902 B2 | 1/2014 | Hammer |
| 8,629,089 B2 | 1/2014 | Dams |
| 8,638,104 B2 | 1/2014 | Barber et al. |
| 8,722,812 B2 | 5/2014 | Yabu et al. |
| 8,877,954 B2 | 11/2014 | Giesenberg et al. |
| 8,996,346 B2 | 3/2015 | Zuo et al. |
| 9,023,966 B2 | 5/2015 | Zhang et al. |
| 9,050,655 B2 | 6/2015 | Chou et al. |
| 9,080,097 B2 | 7/2015 | Gupta et al. |
| 9,121,271 B2 | 9/2015 | Shook |
| 9,133,709 B2 | 9/2015 | Huh et al. |
| 9,200,102 B2 | 12/2015 | Baran, Jr. et al. |
| 9,227,929 B2 | 1/2016 | Winter et al. |
| 9,279,771 B2 | 3/2016 | Aizenberg et al. |
| 9,296,851 B2 | 3/2016 | Luettgen |
| 9,366,099 B2 | 6/2016 | Ly |
| 9,375,790 B2 | 6/2016 | Murphy et al. |
| 9,481,764 B1 | 11/2016 | Kinlen et al. |
| 9,534,062 B2 | 1/2017 | He et al. |
| 9,592,555 B2 | 3/2017 | Schut et al. |
| 9,624,422 B2 | 4/2017 | Dams et al. |
| 9,664,665 B2 | 5/2017 | Gisolf et al. |
| 9,708,525 B2 | 7/2017 | Suresh et al. |
| 9,719,009 B2 | 8/2017 | Jangda et al. |
| 9,809,740 B2 | 11/2017 | Chakraborty et al. |
| 9,873,622 B2 | 1/2018 | Kang et al. |
| 9,873,827 B2 | 1/2018 | Chakraborty et al. |
| 10,273,399 B2 | 4/2019 | Cox |
| 10,308,865 B2 | 6/2019 | Cox |
| 10,308,895 B2 | 6/2019 | Vidal et al. |
| 10,316,873 B2 | 6/2019 | Weitz et al. |
| 10,392,555 B2 | 8/2019 | Giro et al. |
| 10,421,894 B2 | 9/2019 | Johnson et al. |
| 10,487,259 B2 | 11/2019 | Cox |
| 2001/0036667 A1 | 11/2001 | Tayebi |
| 2002/0026000 A1 | 2/2002 | Varadaraj et al. |
| 2003/0220204 A1 | 11/2003 | Baran et al. |
| 2004/0108110 A1 | 6/2004 | Zupanick et al. |
| 2004/0143059 A1 | 7/2004 | Cabrera et al. |
| 2005/0080209 A1 | 4/2005 | Blankenship et al. |
| 2005/0252286 A1 | 11/2005 | Ibrahim et al. |
| 2006/0088476 A1 | 4/2006 | Harder |
| 2006/0105052 A1 | 5/2006 | Acar et al. |
| 2006/0120683 A1 | 6/2006 | Kamp et al. |
| 2007/0114030 A1 | 5/2007 | Todd et al. |
| 2007/0119244 A1 | 5/2007 | Goodwin et al. |
| 2008/0019921 A1 | 1/2008 | Zhang |
| 2008/0110253 A1 | 5/2008 | Stephenson et al. |
| 2008/0111064 A1 | 5/2008 | Andrews et al. |
| 2008/0206317 A1 | 8/2008 | Johnsson et al. |
| 2008/0220970 A1 | 9/2008 | Martin |
| 2009/0087911 A1 | 4/2009 | Rogerio |
| 2009/0087912 A1 | 4/2009 | Ramos et al. |
| 2009/0173253 A1 | 7/2009 | Roesch et al. |
| 2009/0174117 A1 | 7/2009 | Winkler et al. |
| 2009/0248309 A1 | 10/2009 | Nelville et al. |
| 2009/0253595 A1 | 10/2009 | Qu et al. |
| 2009/0277625 A1 | 11/2009 | Bai et al. |
| 2010/0049625 A1 | 2/2010 | Biebesheimer et al. |
| 2010/0068821 A1 | 3/2010 | St Germain |
| 2010/0092865 A1 | 4/2010 | Kanno et al. |
| 2010/0224823 A1 | 9/2010 | Yin et al. |
| 2010/0270020 A1 | 10/2010 | Baran et al. |
| 2010/0290999 A1 | 11/2010 | Kim |
| 2010/0305219 A1 | 12/2010 | Granick et al. |
| 2010/0307745 A1 | 12/2010 | Lafitte |
| 2011/0012331 A1 | 1/2011 | Kim |
| 2011/0030949 A1 | 2/2011 | Weaver et al. |
| 2011/0129424 A1 | 6/2011 | Berkland et al. |
| 2011/0207231 A1 | 8/2011 | Natan et al. |
| 2011/0239754 A1 | 10/2011 | Dyer |
| 2011/0260051 A1 | 10/2011 | Preudhomme et al. |
| 2011/0275061 A1 | 11/2011 | Weidemaier et al. |
| 2011/0320128 A1 | 12/2011 | Shook |
| 2012/0062886 A1 | 3/2012 | Piotti et al. |
| 2012/0115128 A1 | 5/2012 | Miller |
| 2012/0135080 A1 | 5/2012 | Bromberg et al. |
| 2012/0175120 A1 | 7/2012 | Holcomb et al. |
| 2012/0193578 A1 | 8/2012 | Pan et al. |
| 2012/0257199 A1 | 10/2012 | Liu et al. |
| 2012/0261617 A1 | 10/2012 | Pan et al. |
| 2012/0325465 A1 | 12/2012 | Hammer et al. |
| 2013/0040292 A1 | 2/2013 | Lopez et al. |
| 2013/0084630 A1 | 4/2013 | Rolland et al. |
| 2013/0084643 A1 | 4/2013 | Connnnarieu |
| 2013/0087020 A1 | 4/2013 | Brutchey et al. |
| 2013/0087329 A1 | 4/2013 | Hewitt |
| 2013/0087340 A1 | 4/2013 | Choens et al. |
| 2013/0109261 A1 | 5/2013 | Koene |
| 2013/0126158 A1 | 5/2013 | Gupta |
| 2013/0172853 A1 | 7/2013 | McClain |
| 2013/0244914 A1 | 9/2013 | Wu et al. |
| 2013/0259808 A1 | 10/2013 | Chen et al. |
| 2013/0296453 A1 | 11/2013 | Giesenberg et al. |
| 2013/0312970 A1 | 11/2013 | Lafitte et al. |
| 2013/0341030 A1 | 12/2013 | Brannon et al. |
| 2014/0060832 A1 | 3/2014 | Mahoney et al. |
| 2014/0077121 A1 | 3/2014 | Sun et al. |
| 2014/0122047 A1 | 5/2014 | Saldivar et al. |
| 2014/0186939 A1 | 7/2014 | Peterman et al. |
| 2014/0190700 A1 | 7/2014 | Tang et al. |
| 2014/0208825 A1 | 7/2014 | Holba et al. |
| 2014/0231077 A1 | 8/2014 | Rivero et al. |
| 2014/0260694 A1 | 9/2014 | Szlendak |

(56) References Cited

U.S. PATENT DOCUMENTS

| | | | |
|---|---|---|---|
| 2014/0323363 A1 | 10/2014 | Perriat | |
| 2014/0360973 A1 | 12/2014 | Yin et al. | |
| 2015/0001385 A1 | 1/2015 | Perriat et al. | |
| 2015/0013983 A1 | 1/2015 | Alwattari | |
| 2015/0038347 A1 | 2/2015 | Johnson et al. | |
| 2015/0050741 A1 | 2/2015 | Tour et al. | |
| 2015/0079270 A1 | 3/2015 | Wang et al. | |
| 2015/0118501 A1 | 4/2015 | Lu | |
| 2015/0132543 A1 | 5/2015 | Nouzille et al. | |
| 2015/0132742 A1 | 5/2015 | Thou et al. | |
| 2015/0148269 A1 | 5/2015 | Tamsilian | |
| 2015/0153472 A1 | 6/2015 | Tour | |
| 2015/0159079 A1 | 6/2015 | Huh et al. | |
| 2015/0175876 A1 | 6/2015 | Resasco et al. | |
| 2015/0232748 A1 | 8/2015 | Kanj et al. | |
| 2015/0268370 A1 | 9/2015 | Johnston et al. | |
| 2015/0299369 A1 | 10/2015 | Ausserre et al. | |
| 2015/0368547 A1 | 12/2015 | Lesko et al. | |
| 2015/0376493 A1 | 12/2015 | Huh et al. | |
| 2016/0003040 A1 | 1/2016 | Jessheim et al. | |
| 2016/0016166 A1 | 1/2016 | Rolland et al. | |
| 2016/0040514 A1 | 2/2016 | Rahmani et al. | |
| 2016/0061020 A1 | 3/2016 | Sayarpour | |
| 2016/0061790 A1 | 3/2016 | Zhang | |
| 2016/0075937 A1 | 3/2016 | Cannan | |
| 2016/0083641 A1 | 3/2016 | Gamage | |
| 2016/0097750 A1 | 4/2016 | Van Herzen | |
| 2016/0129371 A1 | 5/2016 | Black | |
| 2016/0251571 A1 | 9/2016 | Agrawal et al. | |
| 2016/0264846 A1 | 9/2016 | Bennetzen et al. | |
| 2016/0340569 A1 | 11/2016 | Belcher | |
| 2017/0067322 A1 | 3/2017 | Wong | |
| 2017/0173546 A1 | 6/2017 | Cheng et al. | |
| 2017/0199124 A1 | 7/2017 | Bolduc et al. | |
| 2017/0322202 A1* | 11/2017 | Kobayashi | G01N 33/523 |
| 2018/0275114 A1 | 9/2018 | Kosynkin | |
| 2018/0306709 A1* | 10/2018 | Zaccari | G01N 21/6456 |
| 2018/0369808 A1 | 12/2018 | Wronko | |
| 2019/0016943 A1 | 1/2019 | Ren et al. | |
| 2019/0118175 A1 | 4/2019 | Kim et al. | |
| 2019/0226326 A1 | 7/2019 | Ow et al. | |
| 2019/0368336 A1 | 12/2019 | Hammond et al. | |
| 2020/0116019 A1 | 4/2020 | Ow et al. | |

FOREIGN PATENT DOCUMENTS

| | | | |
|---|---|---|---|
| CN | 102649831 | | 8/2012 |
| CN | 103160265 | | 6/2013 |
| CN | 103267825 | | 8/2013 |
| CN | 103275270 | | 9/2013 |
| CN | 103352255 | | 10/2013 |
| CN | 102586873 | | 12/2014 |
| CN | 104616350 | | 5/2015 |
| CN | 107915802 | | 4/2018 |
| CN | 108614106 | A * | 10/2018 |
| EP | 0171978 | | 11/1990 |
| EP | 1721603 | | 11/2006 |
| EP | 2004573 | | 12/2008 |
| EP | 2040075 | | 3/2009 |
| EP | 2104082 | | 9/2009 |
| EP | 1404776 | | 11/2012 |
| EP | 2480625 | | 4/2013 |
| EP | 2480626 | | 4/2013 |
| EP | 3444028 | | 2/2019 |
| FR | 2756046 | | 5/1998 |
| FR | 2928484 | | 9/2009 |
| GB | 2489714 | | 10/2012 |
| KR | 20170131731 | | 11/2017 |
| KR | 101852925 | | 4/2018 |
| WO | WO 1999038931 | | 8/1999 |
| WO | WO 2002102917 | | 12/2002 |
| WO | WO 2003100214 | | 12/2003 |
| WO | WO 2004095259 | | 11/2004 |
| WO | WO 2007124814 | | 11/2007 |
| WO | WO 2008034553 | | 3/2008 |
| WO | WO 2010138914 | | 12/2010 |
| WO | WO 2011035294 | | 3/2011 |
| WO | WO 2011063023 | | 5/2011 |
| WO | WO 2011081681 | | 7/2011 |
| WO | WO 2011035292 | | 10/2011 |
| WO | WO 2012052148 | | 4/2012 |
| WO | WO 2012154332 | | 11/2012 |
| WO | WO 2012158478 | | 11/2012 |
| WO | WO 2013142869 | | 9/2013 |
| WO | WO 2014014919 | | 1/2014 |
| WO | WO 2014066793 | | 5/2014 |
| WO | WO 2014179020 | | 11/2014 |
| WO | WO 2014207075 | | 12/2014 |
| WO | WO 2015044446 | | 4/2015 |
| WO | WO 2015058206 | | 4/2015 |
| WO | WO 2015097116 | | 7/2015 |
| WO | WO 2015200060 | | 12/2015 |
| WO | WO 2016087397 | | 6/2016 |
| WO | WO 2016174413 | | 11/2016 |
| WO | WO 2017015120 | | 1/2017 |
| WO | WO 2017136641 | | 8/2017 |
| WO | WO 2017164822 | | 9/2017 |
| WO | WO 2017210424 | | 12/2017 |
| WO | WO 2018085504 | | 5/2018 |
| WO | WO 2018175763 | | 9/2018 |
| WO | WO 2018234431 | | 12/2018 |
| WO | WO 2019027817 | | 2/2019 |
| WO | WO 2019063100 | | 4/2019 |

OTHER PUBLICATIONS

USDA, Irrigation and Water Management, Retrieved from https://www.nass.usda.gov/Publications/Highlights/2019/2017Census_Irrigation_and_WaterManagement.pdf (Year: 2018).*

PCT International Search Report and Written Opinion issued in International Application No. PCT/US2020/042295 on Oct. 2, 2020, 21 pages.

Asano et al., "Development of paper-based microfluidic analytical device for iron assay using photomask printed with 3D printer for fabrication of hydrophilic and hydrophobic zones on paper by photolithography," Analytica Chimica Acta, 883:55-60, Apr. 9, 2015, 6 pages.

Agenet et al., "Fluorescent Nanobeads: a First Step Toward Intelligent Water Tracers," SPE-157019, Society of Petroleum Engineers (SPE), presented at the SPE International Oilfield Nanotechnology Conference, Jun. 12-14, 2012, 13 pages.

Alfazazi et al., "Screening of New HPAM Base Polymers for Applications in High Temperature and High Salinity Carbonate Reservoirs," SPE-192805-MS, Society of Petroleum Engineers (SPE), presented at Abu Dhabi International Petroleum Exhibition & Conference, Nov. 12-15, 2018, 17 pages.

Allard and Larpent, "Core-shell type dually fluorescent polymer nanoparticles for ratiometric pH-sensing," J. Polym. Sci., Part A: Polym. Chem. 46:18 (6206-6213), 2008, 8 pages.

Al-Muntasheri et al., "Nanoparticle-Enhanced Hydraulic-Fracturing Fluids: A Review," SPE185161-PA, Society of Petroleum Engineers (SPE), SPE Production & Operations 32:02, May 2017, 10 pages.

Anbari et al., "Microfluidic Model Porous Media: Fabrication and Applications," Nano Micro Small, Special Issue: Multi-Scale Pores and Channels, May 3, 2018, 14:18 (1703575), 15 pages.

Anisimov, "The Use of Tracers for Reservoir Characterization," SPE 118862, Society of Petroleum Engineers (SPE), presented at SPE Middle East Oil and Gas Show and Conference, Mar. 15-18, 2009, 8 pages.

Armelao et al., "Design of luminescent lanthanide complexes: From molecules to highly efficient photo-emitting materials," Coordination Chemistry Reviews, 254: 487-505, Mar. 2010, 19 pages.

Armstrong et al., "Artificial opal photonic crystals and inverse opal structures—fundamentals and applications from optics to energy storage," Journal of Materials Chemistry C, May 2015, 3: 6109-6143, 35 pages.

Asadi et al., "Application of Chemical Tracers in IOR: A Case History," SPE-126029-MS, Society of Petroleum Engineers (SPE),

(56) References Cited

OTHER PUBLICATIONS presented at the SPE North African Technical Conference and Exhibition, Feb. 14-17, 2010, 11 pages.
Aslan et al., "Fluorescent Core—Shell AG@SiO$_2$ Nanocomposites for Metal-Enhanced Fluorescence and Single Nanoparticle Sensing Platforms," JACS Communications, J. Am. Chem. Soc. 129: 1524-1525, Jan. 19, 2007, 2 pages.
Badgett et al., "Totalsynthese eines Neobetanidin-Derivates und des Neobetenamins," Helvetica Chimica Acta, 1970, 53:2 (433-448), 16 pages (English Summary).
Bagaria et al., "Iron Oxide Nanoparticles Grafted with Sulfonated Copolymers are Stable in Concentrated Brine at Elevated Temperatures and Weakly Adsorb on Silica," ACS Applied Materials & Interfaces, 5:8 (3329-3339), Mar. 25, 2013, 11 pages.
Bala et al., "Interaction of Different Metal Ions with Carboxylic Acid Group: A Quantitative Study," The Journal of Physical Chemistry A, 111:28 (6183-6190), Jun. 2007, 8 pages.
Bao et al., "Luminescence properties of the co-luminescence groups of Sm—La-pyridyl carboxylic acids," Journal of Rare Earths, 30:4 (320-324), Apr. 2012, 5 pages.
Behnke et al., "Encapsulation of Hydrophobic Dyes in Polystyrene Micro- and Nanoparticles via Swelling Procedures." J. Fluoresc. 21:3 (937-944), 2011, 8 pages.
Benninger et al., "Time-resolved fluorescence imaging of solvent interaction in microfluidic devices," Optics Express, Sep. 2005, 11 pages.
Borrini et al., "Water Soluble PDCA Derivatives for Selective Ln(III)/An(III) and Am(III)/Cm(III) Separation," Solvent Extraction and Ion Exchange, 33:3 (224-235), Oct. 2014, 30 pages.
Brichart et al., "The Use of Fluorescent Tracers for Inhibitor Concentration Monitoring Useful for Scale Inhibitor," IPTC-17933-MS, International Petroleum Technology Conference (IPTC), presented at the International Petroleum Technology Conference, Dec. 10-12, 2014, 8 pages.
Bunzli and Piguet, "Taking advantage of luminescent lanthanide ions," Chemical Society Reviews, 34:12 (1048-1077), Sep. 2005, 30 pages.
Chang et al., "Magnetic SERS Composite Nanoparticles for Microfluidic Detection," 251st ACE National Meeting, Mar. 13-17, 2016, 1 pages.
Chen et al., "Aggregation Kinetics of Alginate-Coated Hematite Nanoparticles in Monovalent and Divalent Electrolytes," Environmental Science & Technology, 40:5 (1516-1523), Mar. 2006, 8 pages.
Chen et al., "Analysis of the solution conformations of T4 lysozyme by paramagnetic NMR spectroscopy," Royal Society of Chemistry, Physical Chemistry Chemical Physics, 2016, 18:8 (5850-5859), 10 pages.
Chen et al., "Hydration Repulsion between Carbohydrate Surfaces Mediated by Temperature and Specific Ions," Scientific Reports, 6: 1-10, Jun. 23, 2016, 10 pages.
Chen et al., "Impact of Irreversible Retention on Tracer Deployments; Constraining Novel Material Deployments," SPE 188890-MS, Society of Petroleum Engineers (SPE), in SPE Abu Dhabi International Petroleum Exhibition and Conference, Society of Petroleum Engineers, Nov. 13-16, 2017, 8 pages.
Chen et al., "Improved Reservoir History Matching and Production Optimization with Tracer Data," SPE 191523-MS, Society of Petroleum Engineers (SPE), in SPE Annual Technical Conference and Exhibition, Sep. 24-26, 2018, 15 pages.
Chen et al., "Semicontinuous Monomer-Starved Emulsion Polymerization as a Means to Produce Nanolatexes: Analysis of Nucleation Stage," Langmuir, 29: 5650-5658, 2013, 9 pages.
Chen et al., "FITC functionalized magnetic core-shell Fe$_3$O$_4$/Ag hybrid nanoparticle for selective determination of molecular biothiols," Sensors and Actuators B: Chemical 193: 857-863, Dec. 2013, 7 pages.
Christy et al., "Characterization of Natural Organic Matter by Pyrolysis/GC-MS," Environment International, 25, 1999, 9 pages.

Chuang et al., "Ultra-sensitive in-situ detection of novel near-infrared persistent luminescent tracer nanoagents in crude oil-water mixtures," a natureresearch journal, Scientific Reports, Jun. 15, 2016, 5 pages.
Clark et al., "Water-Soluble Fluorochemical Surfactant Well Stimulation Additives," SPE9008, Society of Petroleum Engineers, Journal of Petroleum Technology, 34:07, Jul. 1982, 5 pages.
Coates et al, "Enhancement of luminescence of europium(m) ions in water by use of synergistic chelation. Part 1, 1:1 and 2:1 complexes," J. Chem. Soc, Perkin Trans. 2: 1275-1282, Jan. 1996, 8 pages.
Cole et al., "Polyethylene Glycol Modified, Cross-Linked Starch-Coated Iron Oxide Nanoparticles for Enhanced Magnetic tumor Targeting," Biomaterials, 32:8 (2183-2193), Mar. 1, 2011, 11 pages.
Constantin and Davidson, "Lamellar La Mesophases doped with inorganicnanoparticles," Chemical Phs. Chem. vol. 15, 1270-1282, 2014, 12 pages.
Corning Incorporated, "12.10G1 Fluidic Modules Description," in 09-CD, MG1 HP Instruction Manual, 5 ed.; Corning, Ed. pp. 78-79, 2016, 2 pages.
Corning, "The future flows through Corning Advanced Flow-Reactors," G1 Reactor. Corning, Ed. 2016, 3 pages.
Cox et al., "Pyrolyzable Nanoparticle Tracers for Environmental Interrogation and Monitoring," ACS Appl. Mater. Interfaces 9, 2017, 10 pages.
Cubillos et al., "The Value of Inter-well and Single Well Tracer Technology for De-Risking and Optimizing a CEOR Process—Caracara Field Case," SPE 174394-MS, Society of Petroleum Engineers (SPE), presented at EUROPEC 2015, Jun. 1-4, 2015, 19 pages.
Das et al., "Molecular Fluorescence, Phosphorescence, and Chemiluminescence Spectrometry," Analytical Chemistry, Nov. 3, 2011, 84: 597-625, 29 pages.
Deans, "Using Chemical Tracers To Measure Fractional Flow And Saturation In-Situ," SPE 7076, Society of Petroleum Engineers (SPE), presented at SPE Symposium on improved Methods of Oil Recovery, Apr. 16-17, 1978, 10 pages.
Deschamps et al., "Drilling to the Extreme: the Micro-Coring Bit Concept," IADC/SPE 115187, Society of Petroleum Engineers (SPE), International Association of Drilling Contractors (IADC), presented at the IADC/SPE Asai Pacific Drilling Technology Conference and Exhibition, Aug. 25-27, 2008, 12 pages.
Desmette et al., "Drilling Hard and Abrasive Rock Efficiently, or Generating Quality Cuttings? You No Longer Have to Choose . . . ," SPE 116554, Society of Petroleum Engineers (SPE), presented at the 2008 SPE Annual Technical Conference and Exhibition, Sep. 21-24, 2008, 19 pages.
Doda et al., "Investigation of Alkali Resistant Polymer for Improved Heavy Oil Recovery," SPE 165514, Society of Petroleum Engineers (SPE), presented at SPE Heavy Oil Conference-Canada, Jun. 11-13, 2013, 15 pages.
Du and Guan, "Interwell tracer tests: lessons learned from past field studies," SPE 93140-MS, Society of Petroleum Engineers (SPE), in SPE Asia Pacific Oil and Gas Conference and Exhibition, Society of Petroleum Engineers, Apr. 5-7, 2005, 9 pages.
Duan et al., "Review article: Fabrication of nanofluidic devices," Biomicrofluidics, Mar. 2013, 7:2 (026501), 42 pages.
Dugstad, "Chapter 6: Well-to-well tracer tests," in Petroleum Engineering Handbook, 5, 651-683, 2007, 31 pages.
Edwards et al., "Extending the distance range accessed with continuous wave EPR with Gd3+ spin probes at high magnetic fields," RSC Publishing, Physical Chemistry Chemical Physics (PCCP), 15:27 (11313-11326), 2013, 14 pages.
El-Aneed et al., "Mass Spectrometry, Review of the Basics: Electrospray, MALDI, and Commonly Used Mass Analyzers," Applied Spectroscopy Reviews, Mar. 16, 2009, 44:3 (210-203), 22 pages.
Esmaeilzadeh et al., "Effect of ZrO2 nanoparticles on the interfacial behavior of surfactant solutions at airwater and n-heptane-water interfaces," Fluid Phase Equilibria, 2014, 361, 289-295, 7 pages.
Esumi et al., "Interaction between Zwitterionic Fluorocarbon and Anionic Surfactants in Aqueous Solutions," Langmuir, 9(358-360), 1993, 3 pages.

(56) References Cited

OTHER PUBLICATIONS

Fernández et al., "Evaluation of Cationic Water-Soluble Polymers With Improved Thermal Stability," SPE 93003, presented at SPE International Symposium on Oilfield Chemistry, Society of Petroleum Engineers, Feb. 2005, 13 pages.

Freeze and Cherry, "Chapter 9: Groundwater Contamination," in Groundwater, Englewood Cliffs, NJ: Prentice-Hall, Inc., 1979, 80 pages.

Gaillard et al., "New Water Soluble Anionic NVP Acrylamide Terpolymers for Use in Harsh EOR Conditions," SPE-169108-MS, Society of Petroleum Engineers (SPE), presented at SPE Improved Oil Recovery Symposium, Apr. 12-14, 2014, 18 pages.

Galdiga and Greibrokk, "Ultra-trace determination of flurinated aromatic carboxylic acids in aqueous reservoir fluids using solid-phase extraction in combination with gas chromatography-mass spectrometry," Journal of Chromatography A, 793:2 (267-306), Jan. 16, 1998, 10 pages.

Gao et al., "A Surface Functional Monomer-Directing Strategy for Highly Dense Imprinting of TNT at Surface of Silica Nanoparticles," Journal of American Chemical Society, 129:25 (7859-7866), Jun. 2007, 8 pages.

Gardiner et al., "Chapter 1: Introduction to Raman Scattering," in Practical Raman Spectroscopy, Springer-Verlag, 1989, 9 pages.

George et al., "Modified Dipicolinic Acid Ligands for Sensitation and Europium (III) Luminescence," Inorganic Chemistry, 45:4 (1739-1744), Feb. 1, 2006, 6 pages.

Georgi, et al., "Advances in Cuttings Collection and Analysis," SPWLA 34th Annual Logging Symposium, Jun. 13-16, 1993, 20 pages.

Gerami et al., "Microfluidics for Porous Systems: Fabrication, Microscopy and Applications," Transport in Porous Media, 2019, 130: 277-304, 28 pages.

Goerke et al., "Analysis of the Transfer of Radical Co-polymerisation Systems from Semi-batch to Continuous Plants," in 12th International Symposium on Process Systems Engineering and 25th European Symposium on Computer Aided Process Engineering, Elsevier B.V, Copenhagen, Denmark, 2015, 6 pages.

Gordon-Grossman et al., "W-Band pulse EPR distance measurements in peptides using Gd3+− dipicolinic acid derivatives as spin labels," Physical Chemistry Chemical Physics, 13:22 (10771-10780), 2011, 10 pages.

Greenkorn, "Experimental Study of Waterflood Tracers," Journal Petroleum Technology, SPE-169, 14(1), Jan. 1962, 6 pages.

Grutzke et al., "Heptacoordinate Heteroleptic Salan (ONNO) and Thiosalan (OSSO) Titanium(IV) Complexes: Investigation of Stability and Cytotoxicity," Inorganic Chemistry 54:14 (6697-6706), Jul. 2015, 10 pages.

Hagoot, "The response of interwell tracer tests in watered-out reservoirs," SPE 11131-MS, Society of Petroleum Engineers (SPE), in SPE Annual Technical Conference and Exhibition, Jan. 1982, 21 pages.

Han et al., "Application of Silver-Coated Magnetic Microspheres to a SERS-Based Optofluidic Sensor," The Journal of Physical Chemistry C (JPCC), Mar. 7, 2011, 115: 6290-6296, 7 pages.

He et al., "Luminescent Europium Chelates Synthesis and Fluorescence Properties," Sensors and Materials 2007, 19:2 (123-132), 10 pages.

He et al., "One-pot Facile Synthesis of Janus Particles with Tailored Shape and Functionality," Electronic Supplementary Material (ESI) for Chemical Communications, The Royal Society of Chemistry, 2011, 17 pages.

Hindle et al., "Dipicolinic acid (DPA) assay revisited and appraised for spore detection," Analyst, 1999, 124: 1599-1604, 6 pages.

Holm et al., "Synthesis, Characterization, and Light-Induced Spatial Charge Separation in Janus Graphene Oxide," Chem. Mater. 2018, 30, 2084-2092, 9 pages.

hoteng.com, "Microfluidic Solutions for IOR/EOR Optimisation: Rapid and Cost Efficient EOR Screening using a Rock-On-A-Chip Approach," HOT Engineering GmbH, retrieved from URL <https://www.hoteng.com/microfluidic-solutions/#1457967643112-9de392c4-0c28>, retrieved on Jun. 2, 2020, available on or before Mar. 2019, 8 pages.

Hou et al., "Recent advances in colloidal photonic crystal sensors: Materials, structures and analysis methods," Nano Today, 2018, 22, 132-144, 13 pages.

Hu et al., "Fabrication, properties and applications of Janus particles," Chem. Soc. Rev. 41:11 (4356-4378), 2012, Feb. 2012, 23 pages.

Hu et al., "Smart Liquid SERS Substrates based on $Fe_3O_4$/Au Nanoparticles with Reversibility Tunable Enhancement Factor for Practical Quantitative Detection," a nature research journal, Scientific Reports, Nov. 27, 2014, 4: 7204, 10 pages.

Huseby et al., "Assessing EOR potential from partitioning tracer data," SPE 172808-MS, Society of Petroleum Engineers (SPE), in SPE Middle East Oil and Gas Show and Conference, Mar. 8-11, 2015, 15 pages.

Huseby et al., "High Quality Flow Information from Tracer Data," SPE-169183-MS, Society of Petroleum Engineers (SPE), presented at the SPE Bergen One Day Seminar, Apr. 2, 2014, 9 pages.

Jangda et al., "Evaluation of Fluorosurfactant Performance with Super-Critical CO2 Flooding for High Salinity Carbonate Reservoirs," SPE-169725-MS, Society of Petroleum Engineers (SPE), presented at the SPE EOR Conference at Oil and Gas West Asia, Mar. 2014, 14 pages.

Jenkins et al., "Ultratrace Determination of Selected Lanthanides by Luminescence Enhancement," Analytical Chemistry, 68:17 (2974-2980), Jan. 1, 1996, 7 pages.

Jun et al., "Multifunctional Silver-Embedded Magnetic Nanoparticles as SERS Nanoprobes and Their Applications," Wiley-VCH Verlag GmbH& Co. KGaA, Weinheim, Jan. 4, 2010, 7 pages.

Junkers, "Precision Polymer Design in Microstructured Flow Reactors: Improved Control and First Upscale at Once," Macromol. Chem. Phys. 218: 1600421-1600421, 2016, 9 pages.

Kaushik et al., "Gd(III) and Mn(II) complexes for dynamic nuclear polarization: small molecular chelate polarizing agents and applications with site-directed spin labeling of proteins," Physical Chemistry Chemical Physics, 18:39 (27205-27218), 2016, 36 pages.

Khan et al., "Optimizing waterflood management in a giant UAE carbonate oil field using simulation-based streamlines," SPE 171777-MS, Society of Petroleum Engineers (SPE), presented in the Abu Dhabi International Petroleum Exhibition and Conference, Nov. 10-13, 2014, 9 pages.

Kneipp et al., "Single Molecule Detection Using Surface-Enhanced Raman Scattering (SERS)," Physical Review Letters, American Physical Society 78:9, Mar. 3, 1997, 4 pages.

Knowles et al., "Zwitterion Functionalized Silica Nanoparticle Coatings: The Effect of Particle Size on Protein, Bacteria, and Fungal Spore Adhesion," Langmuir, 35:5 (1335-1345), 2019, 11 pages.

Kong et al., "Microfluidic diatomite analytical devices for illicit drug sensing with ppb-level sensitivity," Sensors and Actuators, B, 259, 2018, 9 pages.

Kornberger and Thiele, "Experiences with an Efficient Rate-Management Approach for the 8th Tortonian Reservoir in the Vienna Basin," SPE 166393-PA, Society of Petroleum Engineers (SPE), SPE Reservoir Evaluation and Engineering, 17:2, May 2014, 12 pages.

Kosynkin and Alaskar, "Oil Industry First Interwell Trial of Reservoir Nanoagent Tracers," SPE 181551-MS, Society of Petroleum Engineers (SPE), presented at the SPE Annual Technical Conference and Exhibition, Sep. 26-28, 2016, 15 pages.

Kramer, "Water-Soluble Dendritic Architectures with Carbohydrate Shells for the Templation and Stabilization of Catalytically Active Metal Nanoparticles," published by ACS, Macromolecules, 38:20 (8308-8315), Aug. 27, 2005, 8 pages.

Kulawardana et al., "Rheology and Transport of Improved EOR Polymers under Harsh Reservoir Conditions," SPE 154294, Society of Petroleum Engineers (SPE), presented at the SPE Improved Oil Recovery Symposium, Apr. 14-18, 2012, 14 pages.

Labbe et al., "Development of metal-chelating inhibitors for the Class II fructose 1,6-bisphosphate (FBP) aldolase," Journal of Inorganic Biochemistry, 112: 49-58, Jul. 2012, 10 pages.

(56) References Cited

OTHER PUBLICATIONS

Larsen et al, "Efficient Synthesis of 4,7-Diamino Substituted 1,10-Phenanthroline-2,9-dicarboxamides," Organic Letters, 13:13 (3546-3548), Jul. 1, 2011, 3 pages.

Levitt et al., "Selection and Screening of Polymers for Enhanced-Oil Recovery," SPE 113845, Society of Petroleum Engineers (SPE), presented at the SPE Symposium on Improved Oil Recovery, Apr. 19-23, 2008, 18 pages.

Li et al., "Magic Angle Spinning NMR Structure Determination of Proteins from Pseudocontact Shifts," Journal of the American Chemical Society (JACS), 135:22 (8294-8303), May 2013, 10 pages.

Li et al., "Thiol—ene reaction: a versatile tool in site-specific labelling of proteins with chemically inert tags for paramagnetic NMR," Chemical Communications, Cambridge, United Kingdom, 48:21 (2704-2706), 2012, 18 pages.

Lomstein and Jorgensen, "Pre-column liquid chromatographic determination of dipicolinic acid from bacterial endospores," Limnology and Oceanography: Methods, Apr. 2012, 10:4 (227-233),14 p.

Luo et al., "Nanofluid of graphene-based amphiphilic Janus nanosheets for tertiary or enhanced oil recovery: High performance at low concentration," PNAS, 2016, 113: 7711-7716, 6 pages.

Luo et al., "Secondary Oil Recovery Using Graphene-Based Amphiphilic Janus Nanosheet Fluid at an Ultralow Concentration," Industrial & Engineering Chemistry Research, Sep. 2017, 56:11125-11132, 25 pages.

Manna et al., "Complexation behavior of trivalent actinides and lanthanides with 1,10-phenanthroline-2,9-dicarboxylic acid based ligands: insight from density functional theory," Physical Chemistry Chemical Physics, 14:31 (11060-1169), Jan. 1, 2012, 10 pages.

Marais et al., "Time-Resolved Fluorescence for Real-Time Monitoring of Both Scale and Corrosion Inhibitors: a Game-Changing Technique," SPE 179867, Society of Petroleum Engineers (SPE), presented at the SPE International Oilfield Scale Conference and Exhibition held in Aberdeen, Scotland, May 11-12, 2016 11 pages.

Marchetti et al., "Fluorous affinity chromatography for enrichment and determination of perfluoroalkyl substances," Annual Review of Analytical Chemistry 84: 7138-7145, Jul. 19, 2012, 8 pages.

Martinez et al., "Chapter 9: Polysaccharide-based Nanoparticles for Controlled Release Formulations," in The Delivery of Nanoparticles, 185-222, May 2012, 39 pages.

Martini et al., "How to Monitor Scale Inhibitor Squeeze using Simple TRF Tracers," SPE-173768-MS, Society of Petroleum Engineers (SPE), presented at the SPE International Symposium on Oilfield Chemistry, Apr. 13-15, 2015, 8 pages.

McGrail et al., "Selective mono-facial modification of grapheneoxide nanosheets in suspension," Chem. Commun, 2016, 52: 288-291, 5 pages.

Melton et al., "Complexes of Greatly Enhanced Thermodynamic Stability and Metal Ion Size-Based Selectivity, Formed by the Highly Preorganized Non-Macrocyclic Ligand 1,10-Phenanthroline-2,9-dicarboxylic Acid: A Thermodynamic and Crystallographic Study," Inorganic Chemistry, 45:23 (9306-9314), Nov. 1, 2006, 9 pages.

micronit.com [online], "Enhanced oil recovery," retrieved from URL <https://www.micronit.com/products/enhanced-oil-recovery.html>, retrieved on Mar. 10, 2020, 5 pages.

Micronit.com, "Lab-on-a-chip and MEMS Solutions," retrieved from URL <https://www.micronit.com/>, retrieved on Jun. 2, 2020, available on or before Mar. 19, 2018 via wayback machine URL <https://web.archive.org/web/20180319182410/https://www.micronit.com/>, 7 pages.

Miller and McQuade, "5 Synthesis of Materials I Flow—Principles and Practice," in De Gruyter et al., Flow Chemistry, 2: 133-160, 2014, Part II, Chapter 5, 28 pages.

Mohamed et al., "Reaction screening in continuous flow reactors," J. Tetrahedron Letters, 57: 3965-3977, 2016, 12 pages.

Morse et al., "Enhanced Reaction Efficiency in Continuous Flow," Isr. J. Chem, 57:218-227, Apr. 2017, 14 pages.

Moyner et al., "The Application of Flow Diagnostics for Reservoir Management," SPE 171557, Society of Petroleum Engineers (SPE), SPE Journal, Apr. 2015, 18 pages.

Muller and Seubert, "Ultra trace determination of fluorobenzoic acids in tap and reservoir water using solid-phase extraction and gas chromatography-mass spectrometry," Journal of Chromatography A, 1260: 9-15, Oct. 2012, 7 pages.

Musyanovych et al., "Preparation of Biodegradable Polymer Nanoparticles by Miniemulsion Technique and Their Cell Interactions," Macromolecular Bioscience, 8:2, Feb. 11, 2008, 13 pages.

Namwong et al., "Fabricating Simple Wax Screen-Printing Paper-Based Analytical Devices to Demonstrate the Concept of Limiting Reagent in Acid-Base Reactions," Journal of Chemical Education 95:2, 2018, 5 page.

Negin et al., "Application of nanotechnology for enhancing oil recovery—A review," Petroleum, 2016, 2: 324-333, 10 pages.

Ng et al., "Graphene-based two-dimensional Janus materials," NPG Asia Materials, 10:4, Apr. 2018, 21 pages.

Nge et al., "Advances in Microfluidic Materials, Functions, Integration, and Applications," Chem. Rev., Apr. 2013, 113:4 (2550-2583), 34 pages.

Nie et al., "Probing Single Molecules and Single Nanoparticles by Surface-Enhanced Raman Scattering," Science, 275:5303 (1102-1106), Feb. 1997, 6 pages.

Nikonov et al., "Development of Remote Gas Condensate Fields: Challenges and Solutions," SPE 176660-MS, Society of Petroleum Engineers (SPE), SPE Russian Petroleum Technology Conference, Oct. 26-28, 2015, published Jan. 1, 2015, 21 pages.

Ogden et al, "Complexation of Am(III) and Nd(in) by 1,10-Phenanthroli ne-2,9-Di carboxylic Acid," Journal of Solution Chemistry, 42:1 (211-225), 2013, 15 pages.

Ouali et al., "Analysis of Paramagnetic NMR Spectra of Triple-Helical Lanthanide Complexes with 2,6-Dipicolinic Acid Revisited: A New Assignment of Structural Changes and Crystal-Field Effects 25 Years Later," Inorganic Chemistry, 41:6 (1436-1445), Feb. 2002, 10 pages.

Pallenberg et al. "Synthesis and Characterization of Some Copper(I) Phenanthroline Complexes" Inorg. Chem. 1995, 34: 2833-2840, 8 pages.

Parker and Williams, "Getting excited about lanthanide complexation chemistry," Journal of the Chemical Society, Dalton Transactions, 18: 3613-3628, 1996, 16 pages.

Parker et al., "Being excited by lanthanide coordination complexes: aqua species, chirality, excited-state chemistry, and exchange dynamics," Chemical Reviews, 102:6 (1977-2010), May 2002, 34 pages.

Peng et al., "A review of nanomaterials for nanofluid enhanced oil and recovery," Royal Society of Chemistry, Jun. 13, 2017, 9 pages.

Petoud et al., "Brilliant SM, Eu, Tb, and Dy Chiral Lanthanide Complexes with Strong Circularly Polarized Luminescence," Journal of the American Chemical Society (JACS), Dec. 15, 2006, J Am. Chem. Soc. 129: 77-83, 2007, 7 pages.

Potapov et al., "Nanometer-Scale Distance Measurements in Proteins Using Gd3+ Spin Labeling," Journal of the American Chemical Society (JACS), 132:26 (9040-9048), Jun. 2010, 9 pages.

Qianming et al., "Bspda Synthesis and its Europium (III) Complexes' Fluorescence," Chemical Industry Times, Jul. 2005, 19:7 (38-41), 4 pages, (English Abstract).

Quadri et al., "Screening of Polymers for EOR in High Temperature, High Salinity and Carbonate Reservoir Conditions," IPTC-18436-MS, presented at the International Petroleum Technology Conference (IPTC), Dec. 6-9, 2015, 30 pages.

Rashadan et al., "Effect of the preparation route, PEG and annealing on the phase stability of Fe3O4 nanoparticles and their magnetic properties," Journal of Experimental Nanoscience, 8:2 (210-222), 2013, 14 pages.

Reese et al., "Synthesis of Highly Charged, Monodisperse Polystyrene Colloidal Particles for the Fabrication of Photonic Crystals," Colloid and Interface Science, 2000, 232: 76-80, 5 pages.

Reisch and Klymchenko, "Fluorescent Polymer Nanoparticles Based on Dyes: Seeking Brighter Tools for Bioimaging." Small 12(15): 1968-1992 2016, 25 pages.

Renault et al., "Three-Dimensional Wax Patterning of Paper Fluidic Devices," Langmuir, 30:23, 2014, 7 pages.

(56) References Cited

OTHER PUBLICATIONS

Rowan et al., "Dynamic Covalent Chemistry," Angewante Chemie International Edition, Mar. 15, 2002, 55 pages.
Sabbatini et al., "Luminescent lanthanide complexes as photochemical supramolecular devices," Coordination Chemistry Reviews, 123:1-2 (201-228), Feb. 1993, 28 pages.
Sabhapondit et al., "Water Soluble Acrylamidomethyl Propane Sulfonate (AMPS) Copolymer as an Enhanced Oil Recovery Chemical," Energy & Fuels, 17:683-688, 2003, 6 pages.
Saeki et al., "Upper and lower critical solution temperatures in poly (ethylene glycol) solutions," Polymer, 17:8, (685-689), Aug. 1976, 5 pages.
Sajjadi, "Nanoparticle Formation by Monomer-Starved Semibatch Emulsion Polymerization," Langmuir, 23: 1018-1024, 2007, 7 pages.
Sajjadi, "Particle Formation under Monomer-Starved Conditions in the Semibatch Emulsion Polymerization of Styrene. I. Experimental.," Journal of Polymer Science: Part A: Polymer Chemistry, 39: 3940-3952, 2001, 13 pages.
Sammes and Yshioglu, "Modern bioassays using metal chelates as luminescent probes," Natural Product Reports, 31:1, 1996, 28 pages.
Sanni et al., "A field case study of inter-well chemical tracer test," SPE-173760-MS, Society of Petroleum Engineers (SPE), presented at the SPE International Symposium on Oilfield Chemistry, Apr. 13-15, 2015, 17 pages.
Sanni et al., "Pushing the envelope of residual oil measurement: A field case study of a new class of inter-well chemical tracers," Journal of Petroleum Science and Engineering, 163, 2018, 19 pages.
Santarelli et al., "Formation Evaluation From Logging on Cuttings," SPE 36851, Society of Petroleum Engineers (SPE), presented at the 1996 SPE Permian Basin Oil and Gas Recovery Conference, Mar. 27-29, 1996, SPE Reservoir Evaluation and Engineering, published Jun. 1998, 7 pages.
Schmidt et al., "Copper dipicolinates as peptidomimetic ligands for the Src SH2 domain," Bioorganic & Medicinal Chemistry Letters, 14:16 (4203-4206), Aug. 2004, 4 pages.
Schmidt et al., "Synthesis of Mono- and Dinuclear Vanadium Complexes and Their Reactivity toward Dehydroperoxidation of Alkyl Hydroperoxides," American Chemical Society (ACS), Inorganic Chemistry 56:3 (1319-1332), 2017, 14 pages.
Seah et al., "Optimizing Recovery in Gas Condensate Reservoirs," SPE 171519-MS, Society of Petroleum Engineers (SPE), SPE Asia Pacific Oil and Gas Conference and Exhibition, Oct. 16, 2014, 19 pages.
Selvin et al., "Principles and biophysical applications of lanthanide-based probes," Annual Review of Biophysics and Biomolecular Structure, 31:275-302, Jun. 2002, 28 pages.
Serres-Piole et al., "Direct sensitive simultaneous determination of fluorinated benzoic acids in oil reservoir waters by ultra high-performance liquid chromatography-tandem mass spectrometry," Journal of Chromatography A, 1218: 5872-5877, Aug. 2011, 6 pages.
Serres-Piole et al., "Water tracers in oilfield applications: Guidelines," Journal of Petroleum Science and Engineering, 98-99: 22-39, Nov. 2012, 18 pages.
ShamsiJazeyi et al., "Polymer-Coated Nanoparticles for Enhance Oil Recovery," Journal of Applied Polymer Science, 131:15, Aug. 5, 2014, 13 pages.
Sharma and Mohanty, "Wettability Alteration in High-temperature and High-salinity Carbonate Reservoirs," SPE Journal, 2013, 18:4 (646-655), 10 pages.
Shook et al., "Determining Reservoir Properties and Flood Performance From Tracer Test Analysis," SPE-124614-MS, Society of Petroleum Engineers (SPE), presented at the 2009 SPE Annual Technology Conference and Exhibition, Oct. 4-7, 2009, 19 pages.
Singh et al., "Paper-based sensors: emerging themes and applications," Sensors, 18:9, 2018, 22 pages.
Sobeih et al., "Recent trends and developments in pyrolysis-gas chromatography," Journal of Chromatography A, 1186:1-2 (51-66), Oct. 11, 2007, 16 pages.
Solomon et al., "Synthesis and Study of Silver Nanoparticles," Journal of Chemical Education 84:2 (332-325), 2007, 4 pages.
Song et al., "SERS-Encoded Nanogapped Plasmonic Nanoparticles: Growth of Metallic Nanoshell by Templating Redox-Active Polymer Brushes," Journal of the American Chemical Society (JACS), Apr. 28, 2014, 136: 6838-6841, 4 pages.
Sriram et al., "Paper-based microfluidic analytical devices for coloimetric detection of toxic ions," Trends in Analytical Chemistry, 93, Jun. 2017, 43 pages.
Stein et al., "Design and functionality of colloidal-crystal-templated materials-chemical applications of inverse opals," Chem. Soc. Rev., 2013, 42: 2763-2803, 41 pages.
Stiles et al., "Surface-Enhanced Raman Spectroscopy," Annual Review of Analytical Chemistry, 1:1 (601-626), Jul. 2008, 29 pages.
Stryer et al., "Diffusion-enhanced fluorescence energy transfer," Annual Review of Biophysics and bioengineering, 11:1 (203-22), 1982, 21 pages.
Su et al., "A Dipicolinic Acid Tag for Rigid Lanthanide Tagging of Proteins and Paramagnetic NMR Spectroscopy," Journal of the American Chemical Society (JACS), 130:32 (10486-10487), Jul. 2008, 2 pages.
Tang et al., "Synthesis and fluorescence properties of Tb(III) complexes with pyridine-2,6-dicarboxylic acid derivatives," Journal of Central South University of Technology (English Edition), 15:5 (599-605), Oct. 2008, 7 pages.
Tang et al., "Synthesis of Novel Derivatives of Pyridine-2,6-dicarboxylic Acid," Synthetic Communications: An International Journal for Rapid Communication of Synthetic Organic Chemistry, 36:14 (2027-2034), Jun. 2006, 9 pages.
Tang et al., "Synthesis of Eu(III) and Tb(III) Complexes with Novel Pyridine-2,6-Dicarboxylic Acid Derivatives and Their Fluorescence Properties," Front. Chem. China, 2006, 4: 408-413, 6 pages.
Taylor et al., "Water-Soluble Hydrophobically Associating Polymers for Improved Oil Recovery: A Literature Review," SPE 29008, Society of Petroleum Engineers (SPE), Journal of Petroleum Science and Engineering, 19:3-4 (265-280), Mar. 1998, 16 pages.
Tian et al., "Off-Resonant Gold Superstructures as Ultrabright Minimally Invasive Surface-Enhanced Raman Scattering (SERS) Probes," American Chemical Society, 27: 5678-5684, Jul. 2015, 7 pages.
Toulhoat, "Experimentation and Modelling of U, Th and Lanthanides Transport in Fissured Rocks: Influence of Complexation," MRS Proceedings, 50, Jan. 1, 1985, 8 pages.
Vaccaro et al., "Flow Approaches Towards Sustainability," Green Chem, 16:3680-3704, 2014, 25 pages.
Vatanparast et al., "Wettability alteration of low-permeable carbonate reservoir rocks in presence of mixed ionic surfactants," Petroleum Sci. Technol., 2011, 29:18 (1873-1884), 14 pages.
Vermolen et al., "Pushing the Envelope for Polymer Flooding Towards High-temperature and High-salinity Reservoirs with Polyacrylamide Based Terpolymers," SPE 141497, Society of Petroleum Engineers (SPE), presented at SPE Middle East Oil and Gas Show and Conference, Mar. 20-23, 2011, 9 pages.
Vollrath et al., "Fluorescence imaging of cancer tissue based on metal-free polymeric nanoparticles—a review." J. Mater. Chem. B 1:15 (1994-2007), 2013, 15 pages.
Wagner, "The Use of Tracers in Diagnosing Interwell Reservoir Heterogeneities—Field Results," SPE-6046, Society of Petroleum Engineers (SPE), Journal of Petroleum Technology, Nov. 1997, 7 pages.
Walther et al, "Janus Particles: Synthesis, Self-Assembly, Physical Properties and Applications," Chem. Rev. 113:7 (5194-5261), Apr. 2013, 68 pages.
Wampler, "Chapter 1: Applied pyrolysis: an overview," Applied Pyrolysis Handbook, 2007, 26 pages.
Wang et al., "The Design and Implementation of a Full Field Inter-Well Tracer Program on a Giant UAE Carbonate Oil Field," SPE-177527-MS, Society of Petroleum Engineers (SPE), presented at the Abu Dhabi International Petroleum Exhibition and Conference, Nov. 9-12, 2015, 8 pages.
Wever et al., "Polymers for enhanced oil recovery: A paradigm for structure—property relationship in aqueous solution," Progress in Polymer Science, 36:11 (1558-1628), Nov. 2011, 71 pages.

(56) References Cited

OTHER PUBLICATIONS

Wu et al., "Development of New Polymers with Better Performance under Conditions of High Temperature and High Salinity," SPE 155653, Society of Petroleum Engineers (SPE), presented at the SPE EOR Conference at Oil and Gas, Apr. 16-18, 2012, 11 pages.
Wu et al., "A reusable biosensor chip for SERS-fluorescence dual mode immunoassay," Proc. SPIE 9543, Third International Symposium on Laser Interaction with Matter (LIMIS 2014), 954317, May 4, 2015, 6 pages.
Wu et al., "A SERS-Assisted 3D Barcode Chip for High-Throughput Biosensing," Small Journal 11:23, Jun. 11, 2015, 9 pages.
Xu et al., "Measurement of two-photon excitation cross sections of molecular fluorophores with data from 690 to 1050 nm," Journal of the Optical Society of America B, 13:3, Mar. 1996, 11 pages.
Yang et al., "The Co-Luminescence Groups of Sm—La-pyridyl Carboxylic Acids and the Binding Characteristics between the Selected Doped Complex and Bovine Serum Albumin," Bulletin of the Korean Chemical Society 33:4 (1303-1309), Apr. 20, 2012, 7 pages.
Yang et al., "Paramagnetic labeling of proteins and pseudocontact shift in structural biology," Chinese Journal of Magnetic Resonance, 2014, 31:2 (155-171), 12 pages (English Abstract).
Ye et al., "Synthesis and Characterization of a Water-Soluble Sulfonates Copolymer of Acrylamide and N-Allylbenzamide as Enhanced Oil Recovery Chemical," Journal of Applied Polymer Science, 128:3, (2003-2011), May 5, 2013, 9 pages.
Zamberi et al., "Improved Reservoir Surveillance Through Injected Tracers In A Saudi Arabian Field: Case Study," SPE 166005, Society of Petroleum Engineers (SPE), presented at SPE Reservoir Characterization and Simulation Conference and Exhibition, Sep. 16-18, 2013, 15 pages.
Zemel, "Chapter 3: Interwell Water Tracers," in Tracers in the Oil Field, Technology and Engineering, Elsevier, 43, Jan. 1995, 47 pages.
Zhang et al., "Effect of Concentration on HPAM Retention in Porous Media," SPE-166265-PA, Society of Petroleum Engineers (SPE), presented as SPE Annual Technical Conference and Exhibition, 373-380, Sep. 30-Oct. 2, 2013, 11 pages.
Zhang et al., "Janus Particles: Synthesis, Self-Assembly, Physical Properties, and Applications," Chem. Rev., 2013, 113: 5194-5261, 14 pages.
Zhang et al., "Novel zwitterionic surfactant derived from castor oil and its performance evaluation for oil recovery," Colloids Surfaces A, 2015, 483: 87-95, 42 pages.
Zhao et al., "Chromatographic Separation of Highly Soluble Diamond Nanoparticles Prepared by Polyglycerol Grafting," Angewandte Chemie International Edition, 50:6 (1388-1392), Feb. 7, 2011, 5 pages.
Zhou et al., "Upconversion luminescent materials: advances and applications," Chem Rev., 115:395-465, Jan. 14, 2015, 71 pages.
GCC Examination Report in Gulf Cooperation Council Appln. No. GC 2020-40115, dated Aug. 31, 2021, 4 pages.
Negin et al., "Most common surfactants employed in chemical enhanced oil recovery," Petroleum, 2017, 3:197-211, 32 pages.

\* cited by examiner

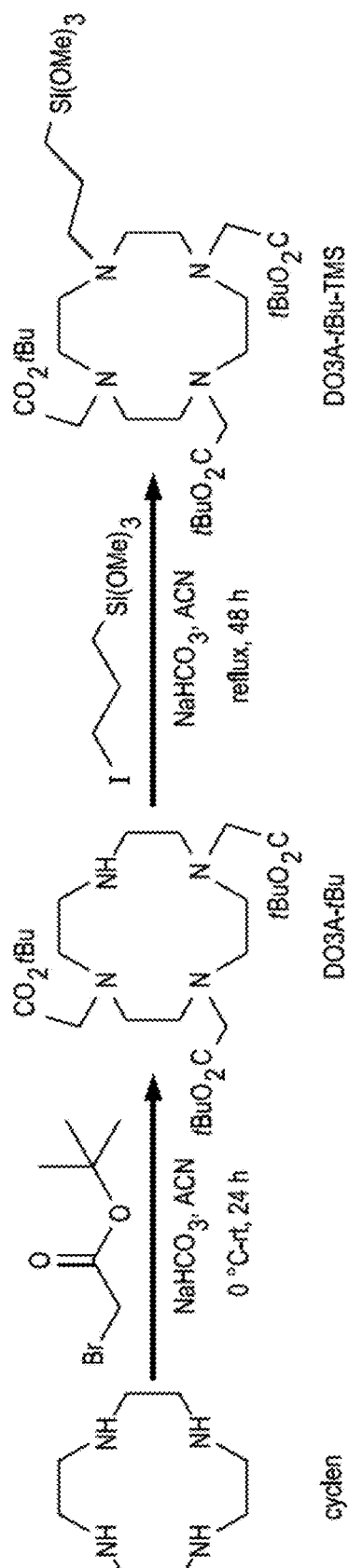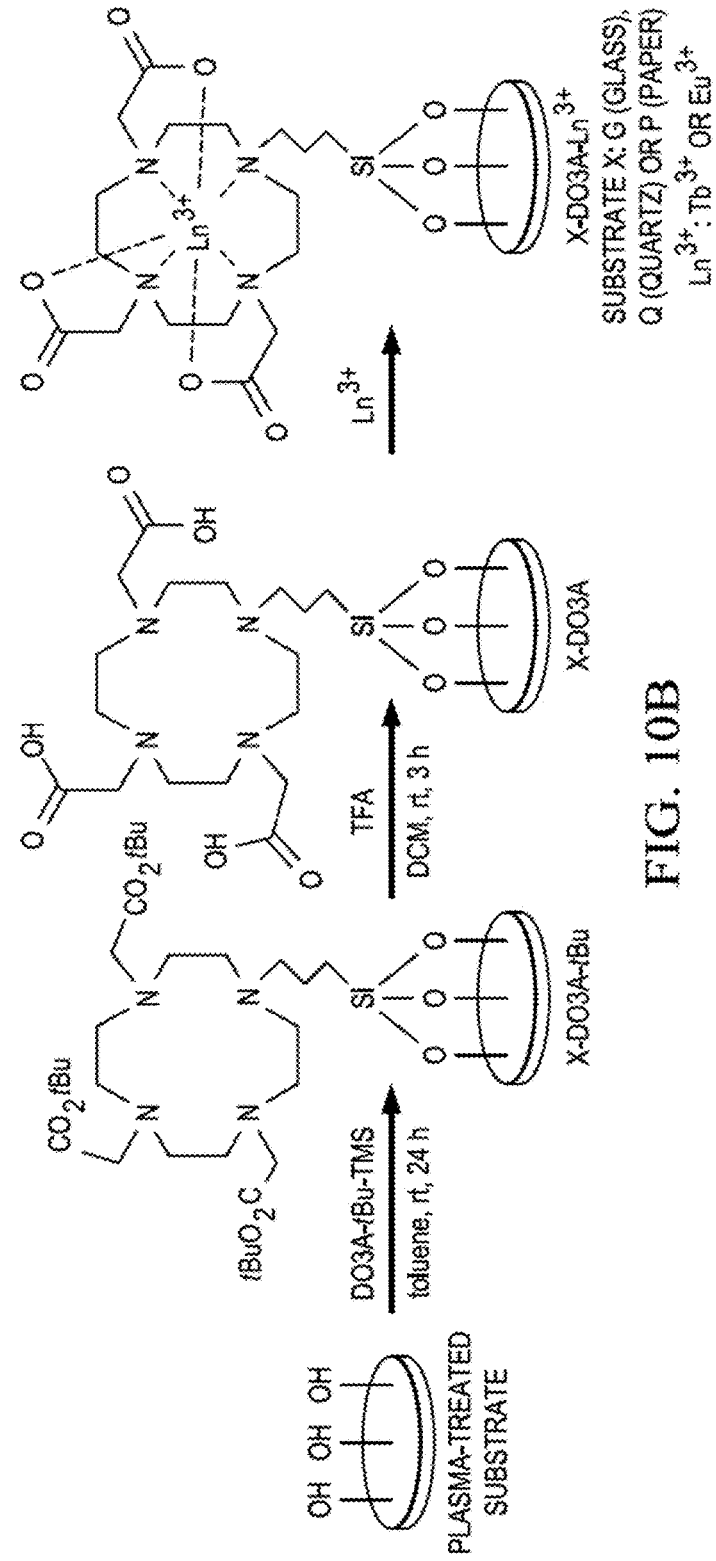
FIG. 10A
FIG. 10B

MULTIPURPOSE MICROFLUIDICS DEVICES FOR RAPID ON-SITE OPTICAL CHEMICAL ANALYSIS

TECHNICAL FIELD

This application relates to microfluidics devices that enable on-site chemical analysis of reservoir fluids in oil fields.

BACKGROUND

Timely detection and quantification of reservoir variables is useful for efficient reservoir management in oil fields. However, reservoir fluid analysis usually requires labor-intensive separation and extraction processes to remove interferents, and the use of sophisticated laboratory instruments that must be operated by trained specialists. These monitoring and surveillance operations are difficult to implement in remote regions.

SUMMARY

This specification describes technologies relating to multipurpose microfluidic devices for rapid on-site optical chemical analysis in oil fields. Paper-based analysis and detection platforms requiring simple hardware can provide near real-time data regarding reservoir variables at the wellsite.

Disclosed are low-cost portable quartz, glass and paper-based diagnostic devices that enable rapid on-site chemical analysis of reservoir fluids to evaluate parameters such as fracturing flowback analysis, trace concentrations, and hydrocarbon composition. Using paper-based devices for trace level fluorescent chemical analysis is challenging, which is effectively addressed with quartz and glass fiber-based substrates. Also described are cost-effective printing methodologies to mass produce these quartz- and glass-based devices using water-based inks augmented with commercially available wax additives. Heat treatment procedures to obtain devices with hydrophobic barriers are also described. Two-sided printing procedures to improve sensitivity of the device also described. This disclosure further describes functionalization chemistries on the quartz and glass substrates to enhance sensitivity of the diagnostic devices as well as outlines fluorimetric or colorimetric read-out or both and quantification methods using a time-resolved fluorescence camera.

The paper-based devices described can be used to perform a coarse oil/water separation, followed by a finer separation achieved using chemical functionalization of a wicking channel that traps or removes salts and organic matter present in the reservoir fluids. This trapping of interferents allows the analytes of interest to bind with reagents on a detection element of the device, leading to the availability of an optical signal that can be read-out with a spectrometer or a camera (such as a steady-state or time-resolved photoluminescence signal).

Fabrication of the devices can be accomplished through printing of paper substrates using solid wax ink printing, wax transfer printing, or silk-screen printing with fabric inks augmented with wax additives. The latter in particular enables printing on non-paperbased fiber substrates such as glass and quartz that could not be fed into conventional solid wax ink office printers. Various printing ink formulations using from about 15 wt % up to about 50 wt % of wax additives to achieve desired hydrophobic properties are disclosed. Further, two-sided printing can be used to fabricate devices that can fully confine aqueous fluids within the device, minimizing or even eliminating crosstalk between devices.

Additionally, outlined are methods for chemical functionalization of quartz, glass or paper substrates to homogenously distribute the detecting reagents on the detection element, minimizing the uneven drying effects from solvent evaporation that could lead to quenching of the fluorescence signal. This improves the robustness and sensitivity of the devices.

In some embodiments, a device for chemical analysis includes a first separation element formed on the substrate, the first separation element having a wicking surface that separates water from hydrocarbons in a fluid sample, a hydrophobic barrier at least partially surrounding the first separation element, a second separation element fluidically connected the first separation element, the second separation element configured to trap salts and organic matter present in the fluid sample, and a detection element fluidically connected to the second separation element, the detection element having a surface that binds with one or more analytes that may be present in the fluid sample and thereby emits a signal that is capable of being optically detected by a detector.

In some aspects of the device, the substrate is quartz, glass, or paper. The second separation element is a channel having a functionalized surface. The hydrophobic barrier is formed by printing ink having wax additives on the substrate followed by heat treatment. The printing ink has from about 15 weight percent (wt %) up to about 50 wt % of wax additives, where the wax additive added up to 50 wt % can be a sunflower-based wax such as Aquacer® 570 and the wax additive up to 15 wt % can be a paraffin-based wax such as Aquacer® 8333. The one or more analyte is dipicolinic acid.

A system for chemical analysis includes any of the devices described above, and a detector configured to detect a signal emitted from the device. In some aspects, the detector is a time-resolved fluorescence camera. The substrate is quartz or glass.

In some embodiments, a method for chemical analysis includes providing a device for chemical analysis that has a first separation element formed on the substrate, the first separation element having a wicking surface that separates water from hydrocarbons in a fluid sample, a hydrophobic barrier at least partially surrounding the first separation element, a second separation element fluidically connected the first separation element, the second separation element configured to trap salts and organic matter present in the fluid sample, and a detection element fluidically connected to the second separation element, the detection element having a surface that binds with one or more analytes that may be present in the fluid sample and thereby emits a signal that is capable of being optically detected by a detector, placing the fluid sample on the first separation element, and detecting the signal emitted by the detection element.

In some aspects of the method, the substrate is quartz, glass, or paper. The second separation element is a channel having a functionalized surface. The hydrophobic barrier is formed by printing ink having wax additives on the substrate followed by heat treatment. The printing ink has from about 15 wt % up to about 50 wt % of wax additives, the wax additive is up to 50 wt % of Aquacer 570 or the wax additive is up to 15 wt % of Aquacer 8333. The one or more analyte is dipicolinic acid.

Particular embodiments of the subject matter described in this specification can be implemented so as to realize one or more of the following advantages. These advantages include simple, fast detection of trace level analytes, and portability and ease of use of the detection devices. Advantageously, devices with tunable confinement (from partial to fully confined) can be produced, allowing, for example, the analyte to be confined to the outermost surface for higher sensitivity detection.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 10A-B show a schematic description of the cyclen derivatization and surface functionalization.

Like reference numbers and designations in the various drawings indicate like elements.

DETAILED DESCRIPTION

In the medical field, microfluidic paper-based analytical devices have been used as a cost-effective, easily accessible, high fidelity platform to diagnose diseases in remote areas where sophisticated instrumentations are inaccessible. Often the read-out of these devices can be done with the naked eye (for positive/negative identification) or quantified easily using portable spectrometers or smart phones with camera capability. Generally, the abundance of the analytes analyzed dictates whether or not detection can be carried out with these simple techniques (such as image processing on a camera phone). For some of the analytes of interest in reservoir fluids, use of such techniques is not possible due to low analyte concentration. Analytes of interest are usually detected in trace or ultra-trace levels, due to the large dilution factor during fluid transport from well to well. Apart from low concentrations, other major challenges of detecting analytes of interest in reservoir fluids using optical methods include the presence of many interferents (such as salts, dissolved organic matter, etc.) in the fluids that can obfuscate the optical signals from the analyte(s). For trace or ultra-trace level optical detection, the background fluorescence, attributable to either fluorescent optical brightener or indigenous lignin in the paper/cellulose fibers, significantly limits the sensitivity.

Figure 1:
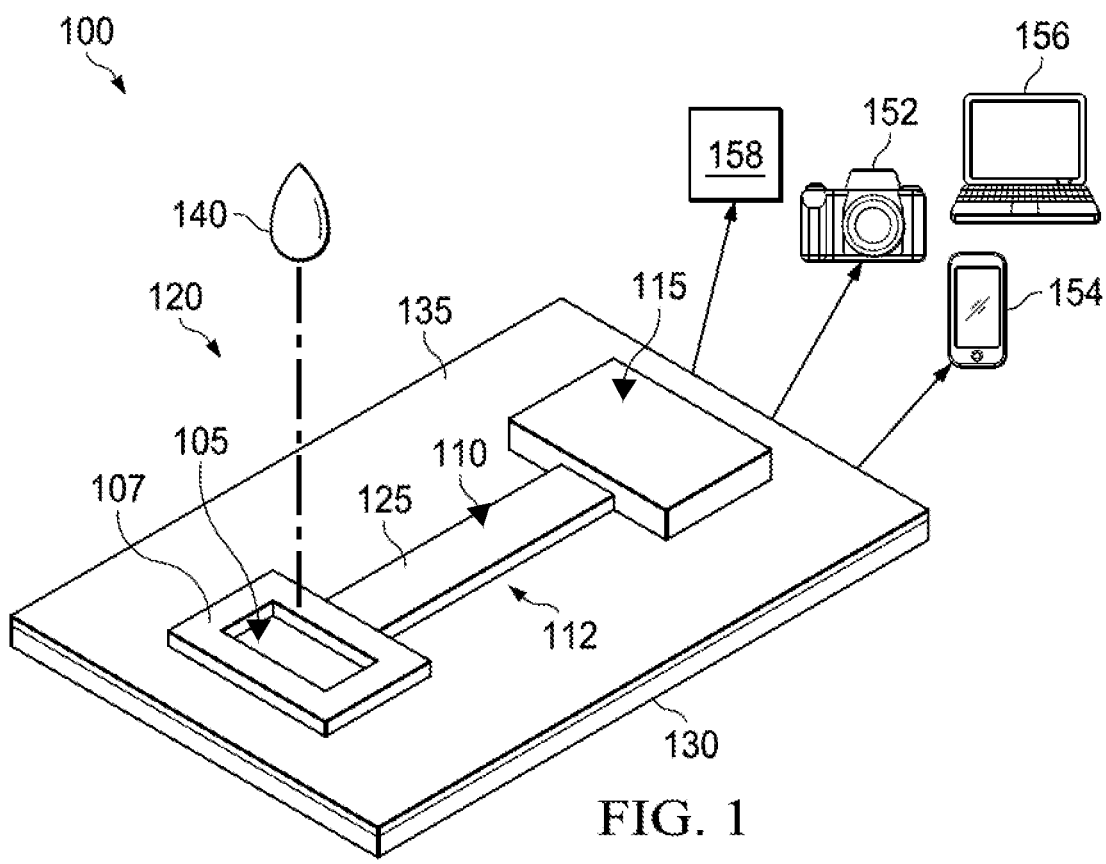
FIG. 1 shows the architecture of an optical-based sensor chip system.
Figure 2A:
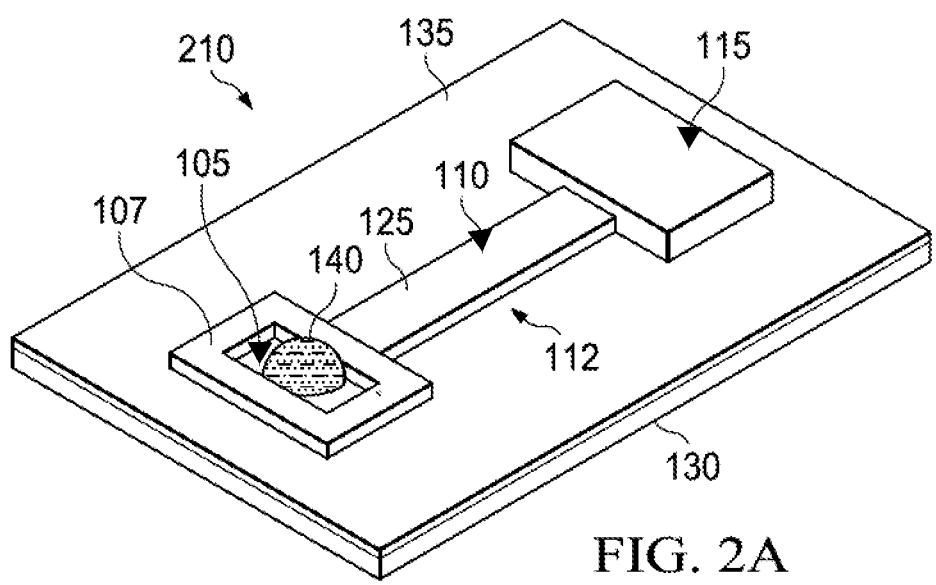
FIGS. 2A-D illustrates the principle of operation of the optical-based sensor chip of FIG. 1.
Figure 2B:
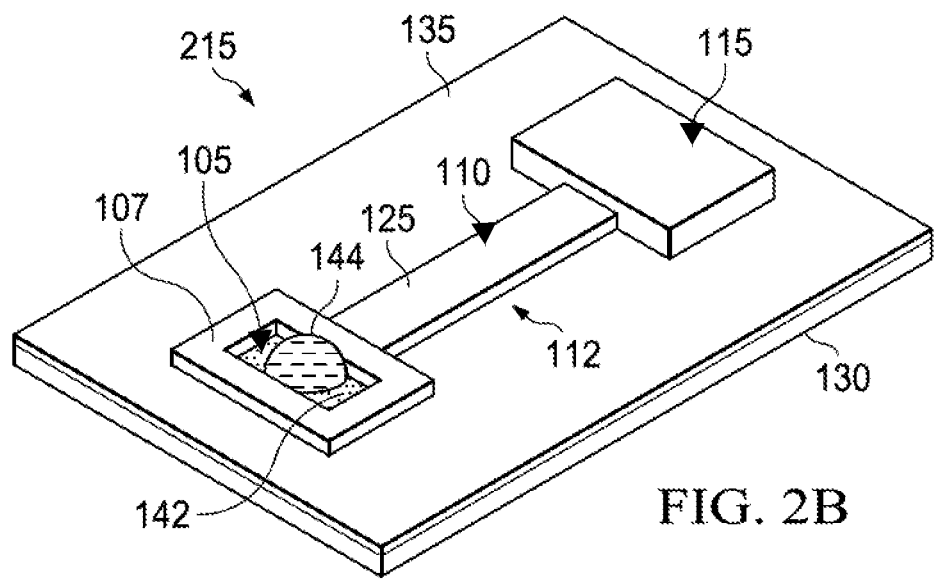
Figure 2C:
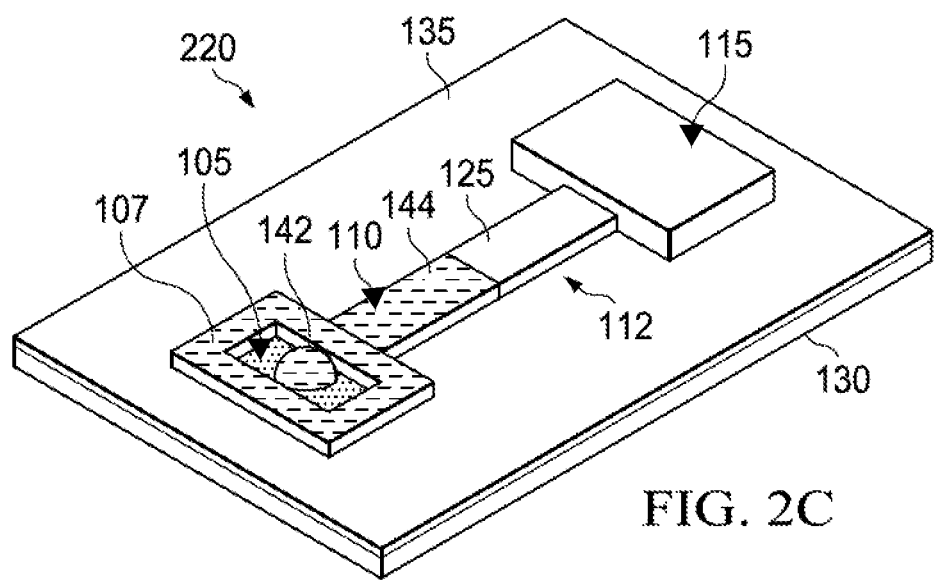
Figure 2D:
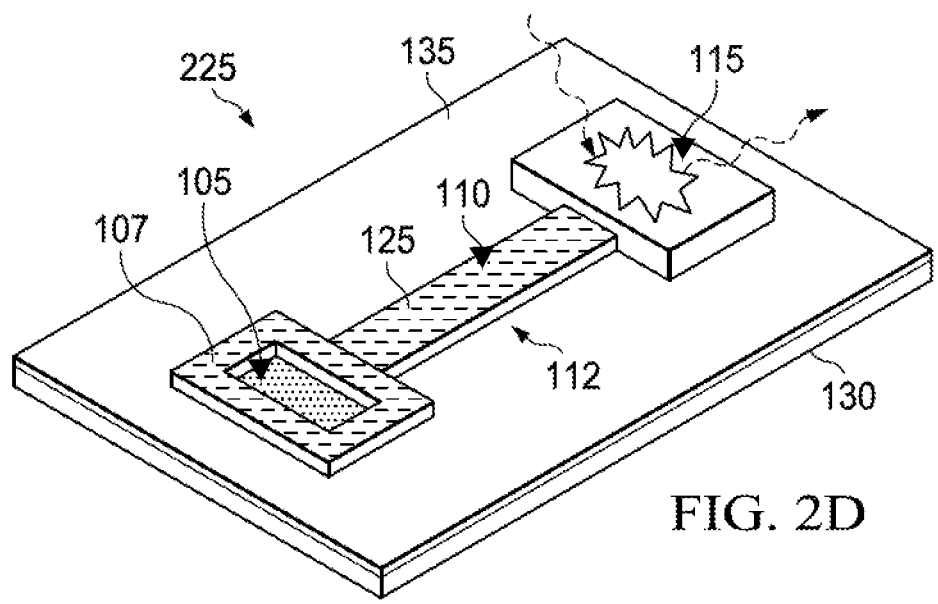
Figure 3A:
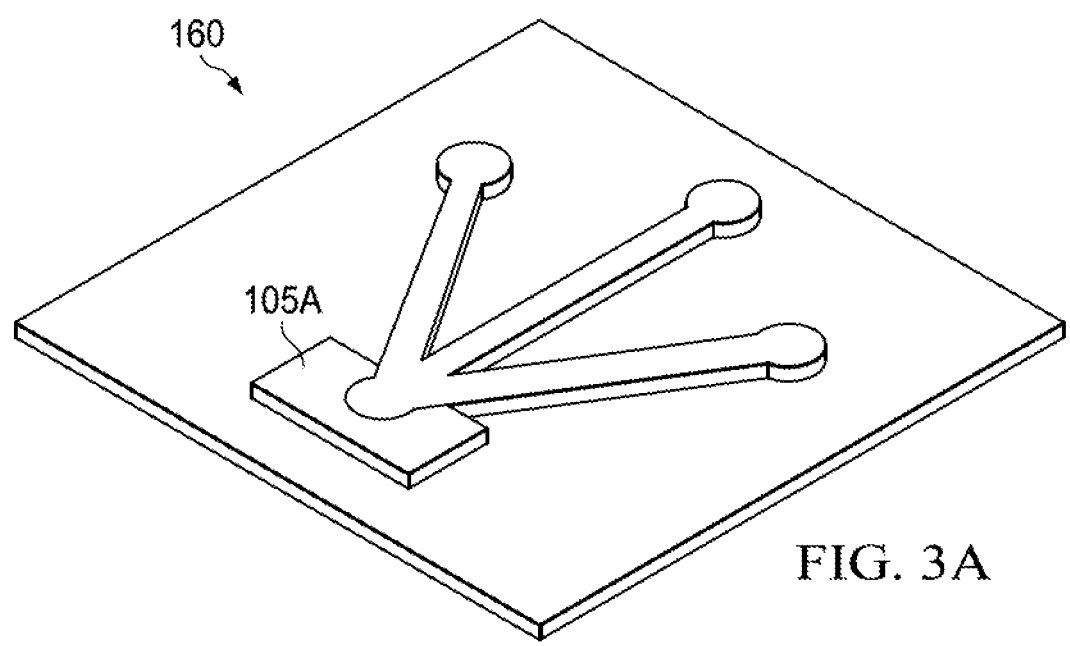
FIGS. 3A-E show a multiplexed sensor chip capable of simultaneous detection of multiple analytes.
Figure 3B:
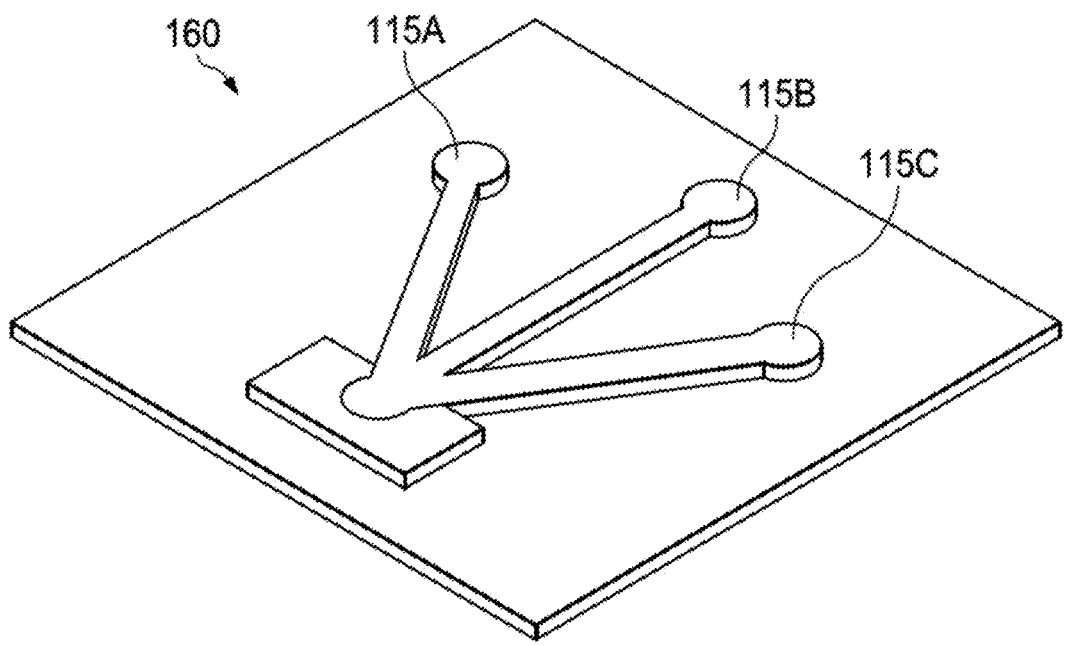
Figure 3C:
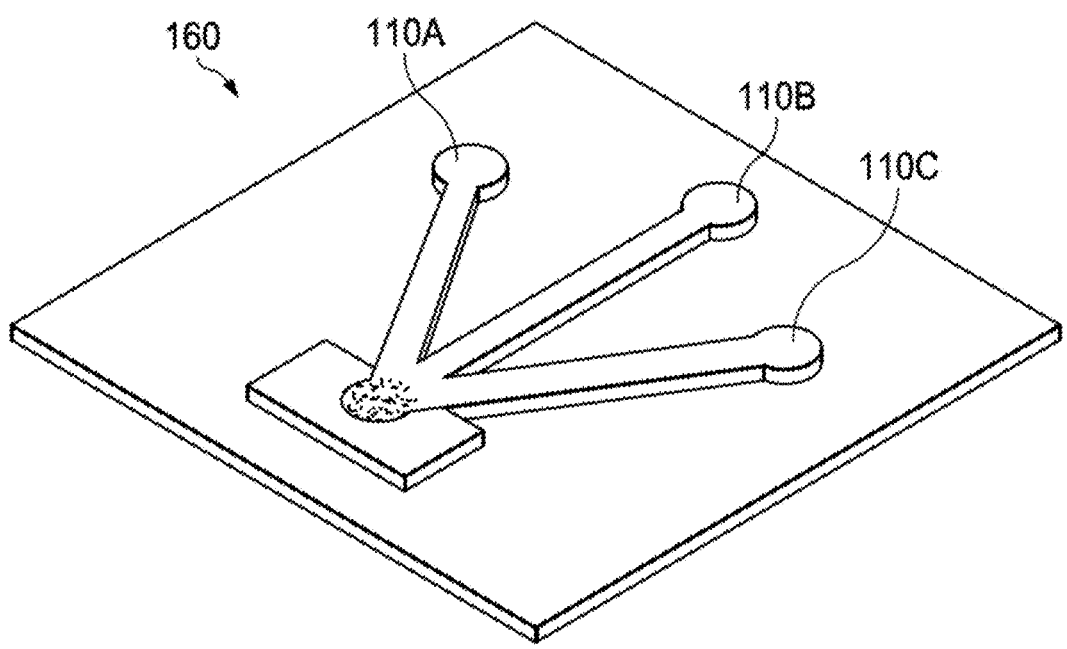
Figure 3D:
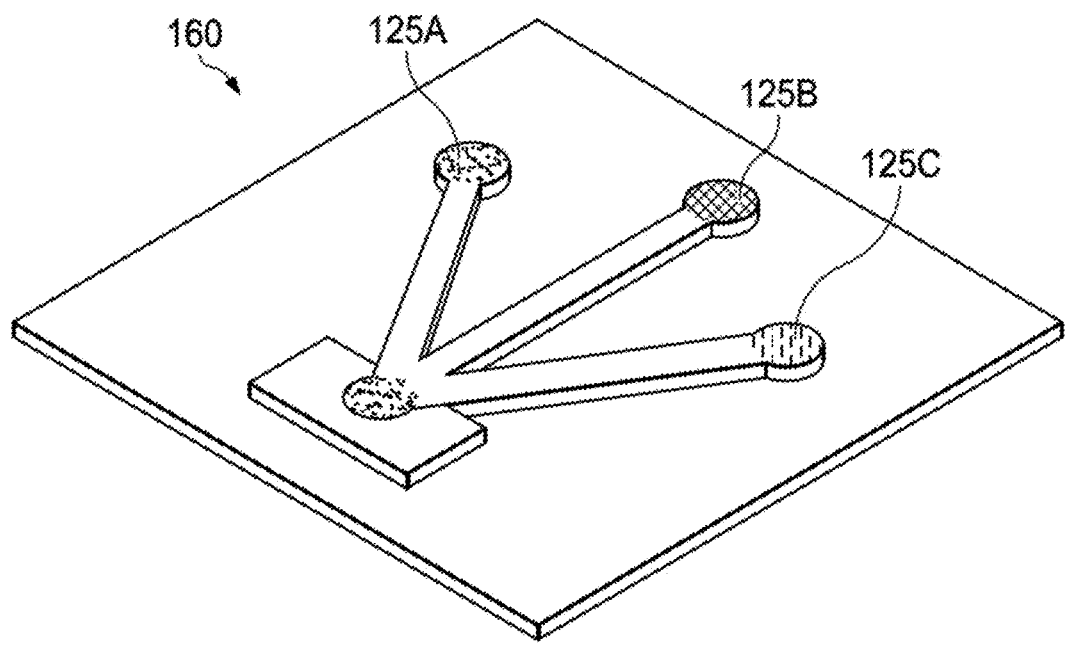
Figure 3E:
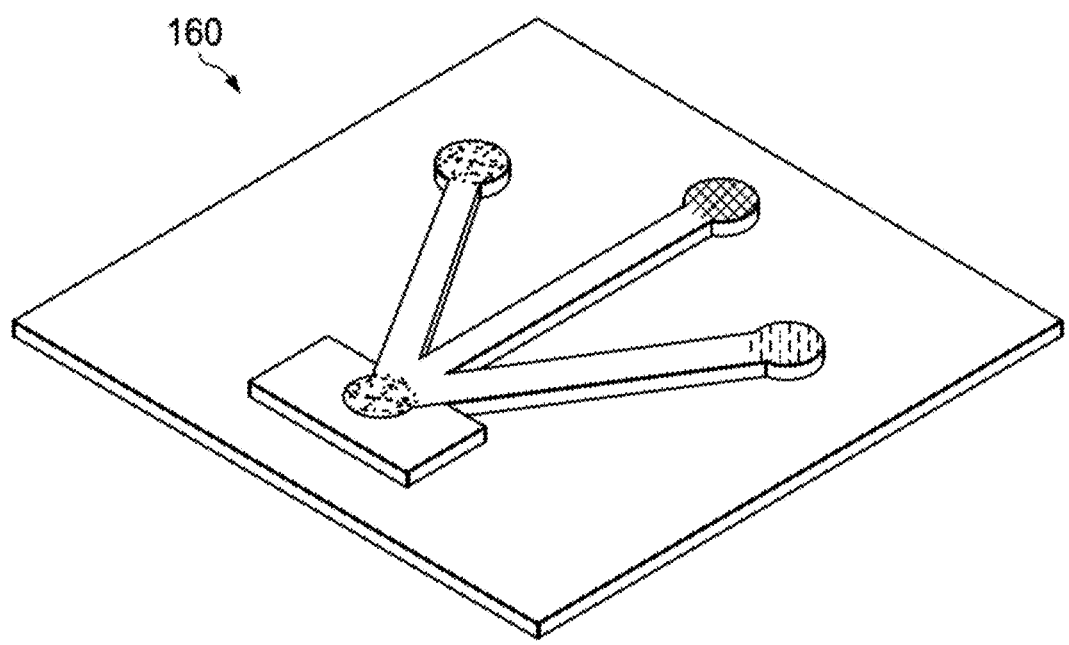

FIG. 1 shows a paper-based diagnostics system 100 for rapid chemical analysis of reservoir fluids in oil fields. The diagnostics system 100 uses a device 120 that has an optical-based sensor chip 130 for the detection of analytes. A sample 140 is placed onto the chip 100, and any signal emitting from the chip 100 is detected by a detector such as a camera 152, smartphone 154, or other device 158 such as a spectrometer. The detected signal is then analyzed and processed by a processor 156, to determine whether or not the analyte of interest is present in the sample 140.

The architecture of the sensor chip 100 includes three main components: a first separation element 105, a second separation element 110 and detection element 115. The first separation element 105 is a hydrophobic surface that can be made with a wax-based printing ink. The first separation element 105 has a hydrophilic channel with a hydrophobic border 107 that causes any oil in the sample 140 to remain with the area outlined by the hydrophobic border 107. Depositing a sample 140 of reservoir fluid on the first separation element 105 causes a first oil/water separation. This separation is coarse, and separates the hydrocarbons and water in the sample 140.

The second separation element 110 is a channel 112 that is fluidically connected to the first separation element 105. The second separation element 110 performs a finer separation than the first separation element 105. The second separation element 110 has the form of a wicking channel and has a chemically functionalized surface 125. The functionalized surface 125 traps or removes organic matter from the coarsely separated fluid as it travels down the channel, desalts the fluid, or chromatographically separates the materials in the fluid such that a particular analyte will preferentially wick toward the detection element 115, or some combination of these actions.

The detection element 115 is at the other end of and fluidically connected with the second separation element 110. The detection element 115 contains a compound or material that can be turned on colorimetrically or fluorescently when the particular analyte, if present in the sample, binds with it. The read-out of the detection element 115 can be done through a steady-state or time-gated fluorescence camera, or a hand-held portable spectrometer that can quantify fluorescence or color intensity.

The three components of the chip 100, the first separation element 105, second separation element 110, and detection element 115, are located on a substrate 135 that forms the backing of the chip 130. The substrate 135 can be quartz, glass, or paper-based.

FIGS. 2A-D schematically illustrate the principle of operation for the optical-based sensor chip 100. First, in step 210, a fluid sample 140 in the form of an oil/water emulsion droplet is placed in the sampling area, being the first separation element 105. The oil 142 from the sample wets the material of the first separation element 105, and the water 144 from the sample beads up due to the hydrophobicity of the material of the first separation element 105, step 215. The water 144 droplet contacts the hydrophilic channel with a hydrophobic border 107 of the first separation element 105, and begins to move down the channel 112 of the second separation element 110, driven by capillary action, step 220. The oil 142 remains in the first separation element 105. The functionalized surface using hydrophobic materials such as C18, C8, fluorinated silanes and fluoropolymers, etc. 125 can trap various interferents as the water 144 moves down the channel 112 of the second separation element 110. And the functionalization of materials such as ethylenediaminetetraacetic acid, or macrocyclic compounds such as 1,4,7,10-Tetraazacyclododecane-1,7-diacetic acid (DO2A), 1,4,7,10-Tetraazacyclododecane-1,4,7-triacetic acid trisodium salt (DO3A), 1,4,7,10-Tetraazacyclododecane-1,4,7,10-tetraacetic acid (DOTA), 1,4,7,10-Tetrakis(carbamoylmethyl)-1,4,7,10-tetraazacyclododecane (DOTAM) etc., on the detection element 115 can immobilize the lanthanide ions for detection.

The water 144 eventually reaches the detection element 115, step 225. Here, tracer elements in the water, if present, react with compounds on the detection element 115, and become luminescent. The compounds can be antenna ligands in a film that forms the detection element 115. The luminescence can be detected by a smartphone 154 shown in FIG. 1, and analyzed to give a final result.

FIGS. 3A-E show an example of an optical-based multiplex sensor chip 160 that uses multiple detection elements 115A, 115B, 115C to analyze a single fluid sample of reservoir fluid. The sensor chip 160 is functionally similar to the sensor chip 130 of FIG. 1, having a first separation element 105. The fluid sample is placed at the single first separation element 105A.

The multiplex sensor chip 160 has multiple second separation elements 110A, 110B, 110C. Each of the second separation elements 110A, 110B, 110C can have different functionalized surfaces 125A, 125B, 125C that react with different compounds and so separate the components of the sample. The different components of the sample each travels to respective detection elements 115A, 115B, 115C. Each detection element 115A, 115B, 115C can have a different material that binds with a different compound, and luminesces. The presence or absence of an analyte can be deduced from whether a respective detection element 115A, 115B, 115C is turned on. The multiplex sensor chip 160 allows multiple analytes in the reservoir fluid sample to be detected simultaneously. Although three different second separation elements 110A, 110B, 110C and detection elements 115A, 115B, 115C are shown, other configurations are possible. Two, four, five or more separation elements and detection elements can be present on a single device 120.

EXAMPLES

Fluorescent detection of either dipicolinic acid (DPA) or 4,7-bissulfonate phenyl-1,10-bisphenyl-phenanthroline-2,9-dicarboxylic acid (BSPPDA) will be used throughout this disclosure as an example of an analyte detectable in reservoir fluids. Nonetheless, it should be understood that other analytes of interest in reservoir fluids, such as concentrations of specific ions in the brine, presence of hydrogen disulfide, or different components of crude oil, can also be detected using the sensor chip described.

Figure 4A:
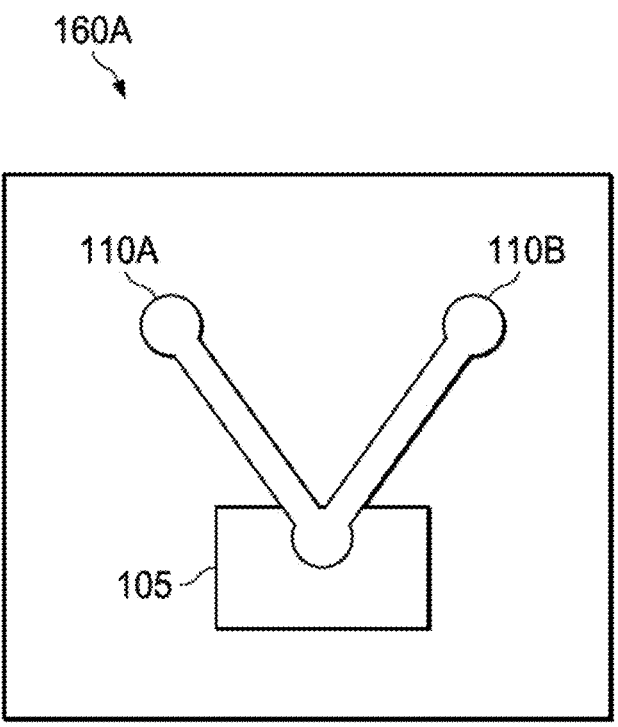
FIGS. 4A-B show another example of a multiplexed sensor chip.
Figure 4B:
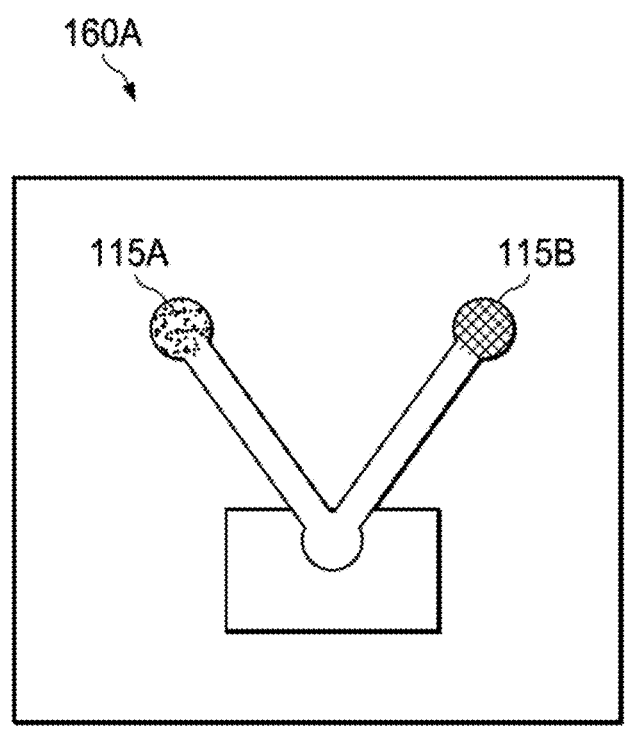

FIGS. 4A-B illustrate example results of detection of DPA tracer on a multiplexed sensor chip 160A. The multiplexed sensor chip 160A in this example has two second separation elements 110A, 110B and two detection elements 115A, 115B.

5 μM of 1 mM of europium chloride and of terbium chloride solution in deionized water was deposited onto the detection elements 115A, 115B of the sensor chip 160A, and allowed to dry so as to form the binding surfaces of the detection elements 115A, 115B. The detection elements 115A, 115B thus contained europium and terbium ions, respectively.

20 μL of water containing 10 ppm (parts-per-million, mass fraction) of DPA was dropped on the first separation element 105 of the device 160A, and allowed to wick up the channels of the second separation elements 115A, 115B. Upon binding with the lanthanide ions, either terbium or europium, a fluorescence turn-on was observed under UV excitation. Detection of the analyte of interest in the fluid, DPA, was detected by the fluorescence of both of the lanthanide ions.

Chromatography paper-based substrates are a convenient canvas to fabricate detection devices. However, for trace-level fluorometric analysis methods, the indigenous lignin content of paper fibers in high purity paper substrates causes background fluorescence, particularly if UV excitation sources are used for the read-out. The example above shown in FIGS. 4A-B illustrates the detection of DPA tracer at 10 ppm. Detection of concentrations lower than 1 ppm would be completely obfuscated by the background fluorescence from the paper substrate.

Figure 5A:
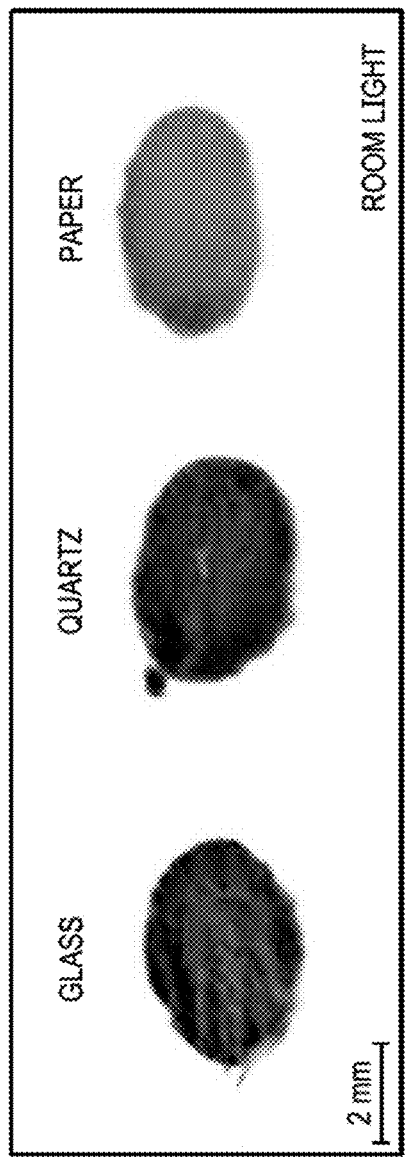
FIGS. 5A-B demonstrate experimental results of background fluorescence levels of three different substrates.
Figure 5B:

FIGS. 5A-B demonstrate background fluorescence level of three different substrates tested. Shown is the background fluorescence of three different possible substrates, glass, quartz and paper, under room light (top panel) and UV illumination (bottom panel). Under UV illumination the background signal observed from high purity chromatography paper is higher than that observed for glass or quartz fiber substrates (a brighter blue signal from the paper substrate). Quartz and glass appear to have the lowest fluorescence. Therefore, for trace level fluorescent detection of analytes in reservoir fluids, either quartz or glass based substrates provide a better platform for the devices.

Paper-based substrate is still useful in colorimetric read-outs of in the cases where the analytes are not expected in trace amounts.

To compare the performance of trace level fluorescence detection of tracers, a six-spot device was constructed. 10 μL of 1E-5M of terbium chloride in 1M sodium acetate buffer was deposited onto each detection element. Then, 10 μL of DPA tracer solution in DI water at concentrations ranging from 1 ppm to 100 ppt (parts-per-trillion, mass fraction) (1 ppm, 100 ppb or 100 parts-per-billion in mass fraction, 10 ppb, 1 ppb, and 100 ppt) was dropped directly onto the detection elements. The control spot contains only the terbium chloride at 1E-5M. These devices were imaged using a Princeton Instruments PI-Max4 ICCD time-resolved fluorescence camera, excited with a 290 nm pulsed LED light source. The objective was to observe a discernable intensity difference between the control spot and the detection element spots containing various amounts of tracers.

Figure 6A:
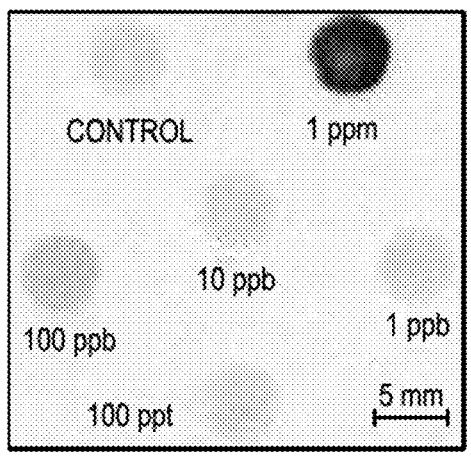
FIGS. 6A-C show experimental results of a comparison of the performance of three different substrates for trace-level optical detection of an analyte, glass, quartz, and paper.
Figure 6B:
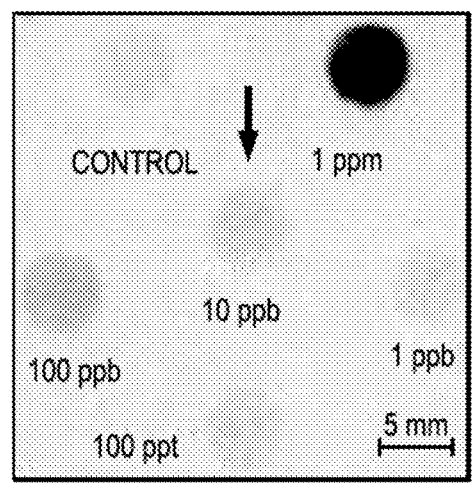
Figure 6C:
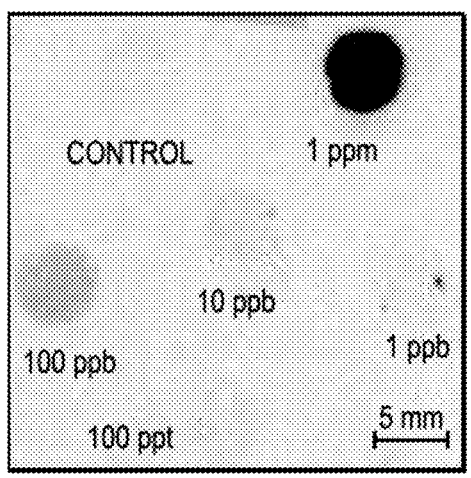

FIGS. 6A-C show the results. The lowest detectable tracer concentration was at 10 ppb on devices made with quartz, whereas the lowest detectable levels of DPA tracer for both paper and glass substrates were at 100 ppb. A comparison of the performance of three different substrates (glass, quartz, and paper) for trace-level optical detection of an analyte shows that quartz-based devices exhibit the lowest limit of detection for fluorescence-based analysis, as indicated by the red arrow.

In some embodiments, the chip 120, 160 could be printed using wax inks via conventional printing techniques (such as using an office printer, silk-screening, wax-transfer printing, 2D ink-jet printing, etc.). Once printed, the wax can be subjected to a brief heat treatment to allow the wax to melt and wick through the substrate by capillary force, thereby creating hydrophobic barriers.

One of the advantages of using chromatography-grade papers as a substrate is that the fabrication of the paper-based devices could be carried out using a solid wax ink office printer, such as the ColorQube® line of printers from Xerox®. However, glass-fiber or quartz-fiber based substrates are not compatible with these printers. To maintain simple and inexpensive device manufacturing techniques for the quartz- and glass-fiber based devices, silk screen printing can be used to print the devices at high throughput.

Testing was carried out with commercial water-based silk-screen inks, in this instance Speedball water-based fabric screen printing inks with wax additives (using Aquacer 8333 and Aquacer 570 from BYK). The experimental objective was to obtain hydrophobic barriers that would confine the aqueous phase of reservoir fluids within the separation elements of the device and prevent or minimize cross-talk between detection elements on a multiplexed sensor chip.

Figure 7A:
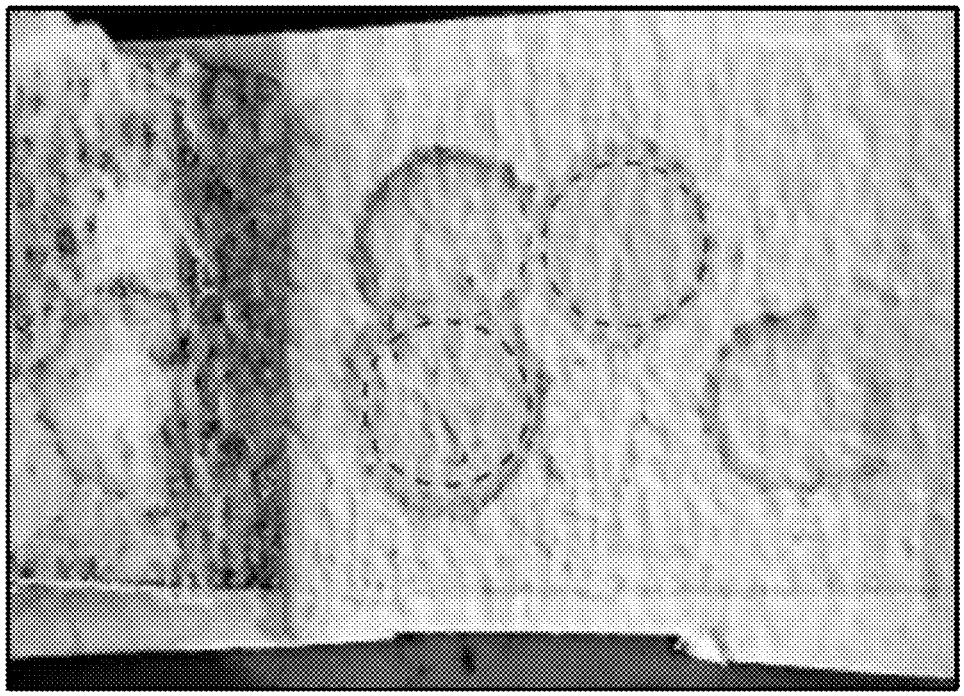
FIGS. 7A-B show experimental results of heat treatments for silk-screen printed devices on quartz substrates.
Figure 7B:
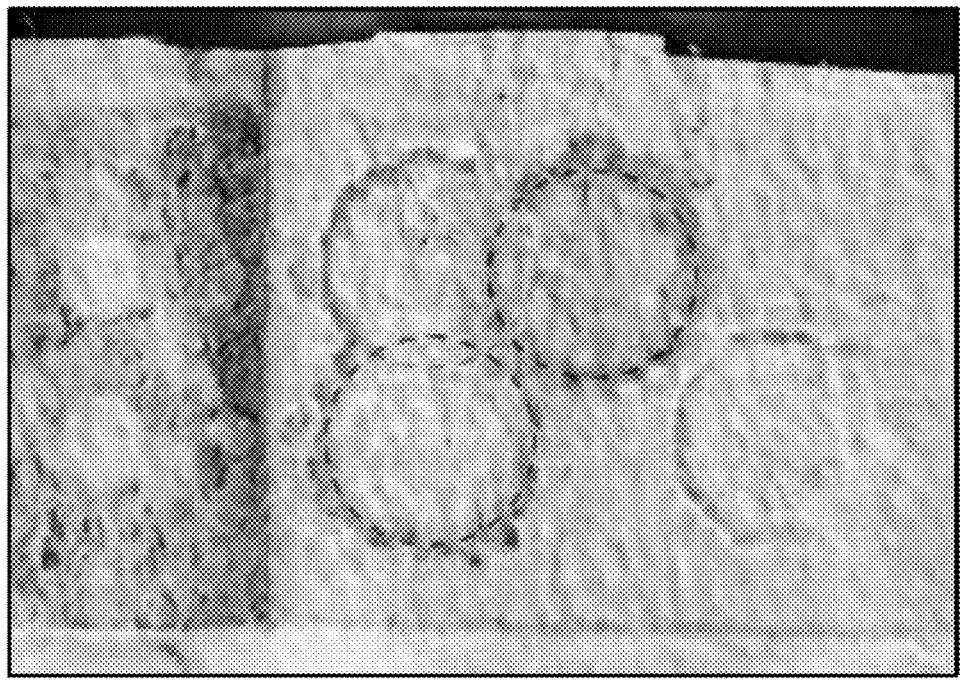
Figure 8A:
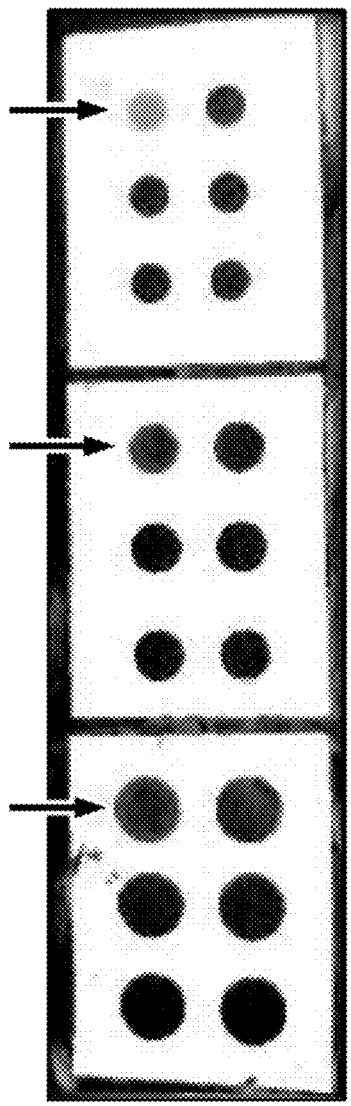
FIGS. 8A-B show experimental results of results of a 1-hour heat experiment.
Figure 8B:
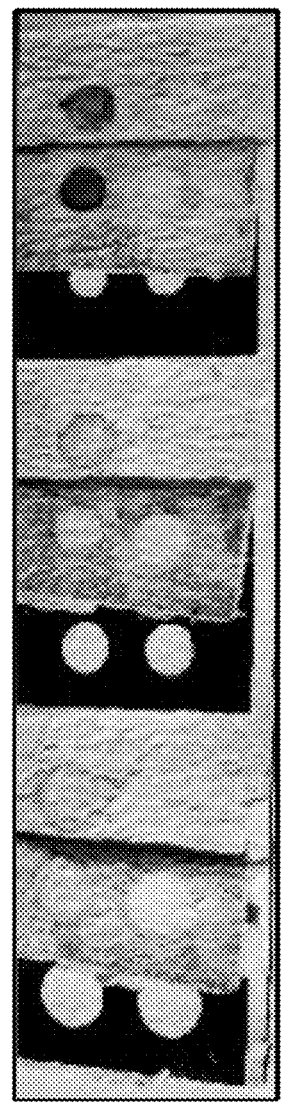

FIGS. 7A-B show results from heat treatments of 25 minutes (left) and 50 minutes (right) for silk-screen printed devices on quartz substrates. The devices were made with 50 wt % Aquacer 570 wax additive in the fabric printing ink. The longer duration was shown to produce better confinement. FIGS. 8A-B show the results of one hour heat treatment on silk-screen printed devices on quartz substrates. Using 15 wt % of Aquacer 8333 wax additive produced the best confinement. Heat treatment is applied in an oven at 80° C. to 100° C., at 95° C., etc.

For the wax additive Aquacer 570, up to 50 wt % of additives was added to produce hydrophobic barriers that prevent crosstalk. For Aquacer 8333, 15 wt % of additive was enough to produce hydrophobic barrier after heat treatment. In each of these cases, post-printing heat-treatment of 1 hour was sufficient to produce hydrophobic barriers from the inks with wax additives.

Figure 9:
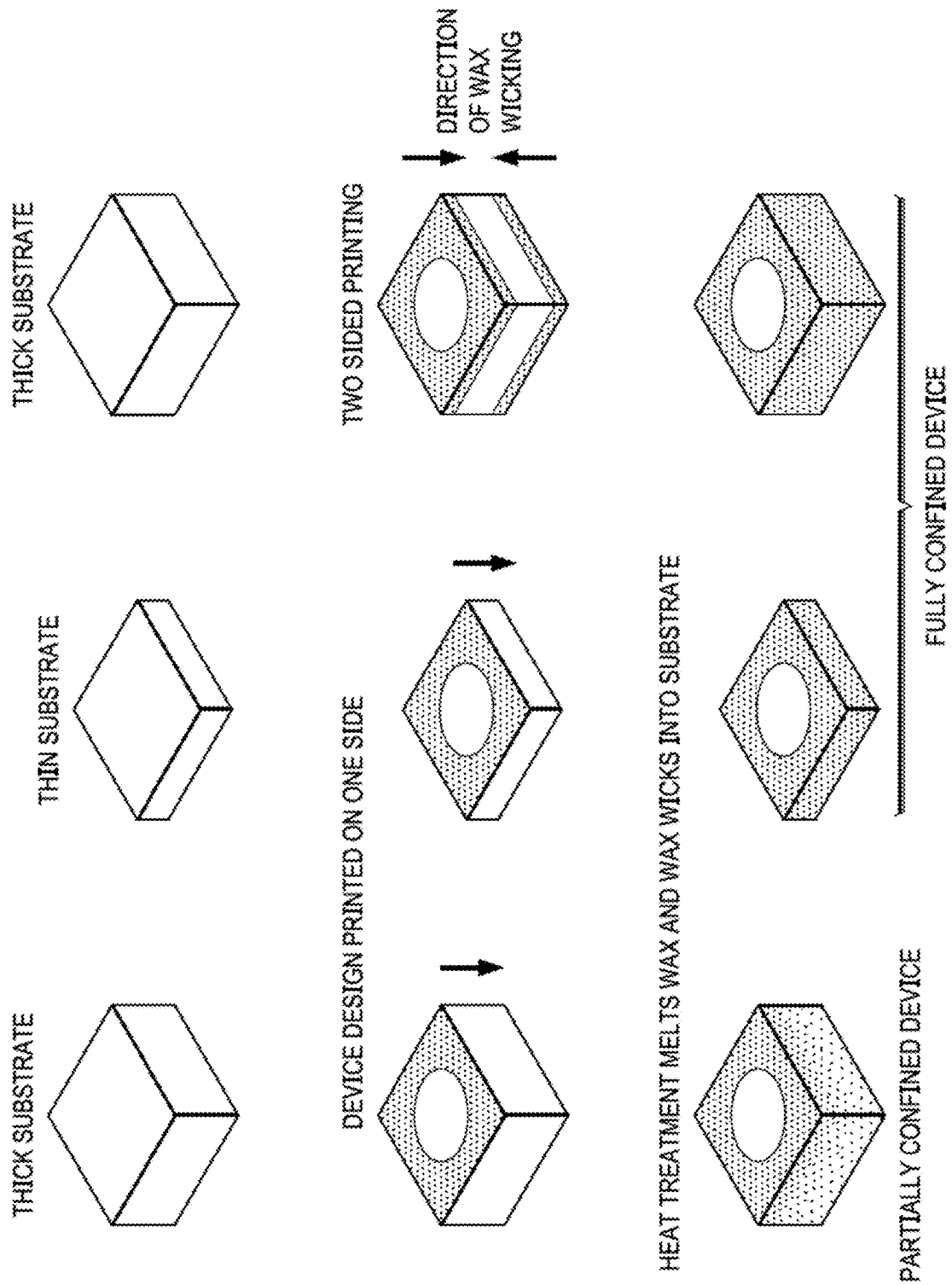
FIG. 9 is a schematic explaining the advantages of two-sided printing.

FIG. 9 shows a schematic explanation of a two-sided printing process that produces fully confined devices with improved performance. Two-sided printing on thicker substrates, such as glass or quartz, enables fully confined detection elements with minimal leakage or crosstalk between detection elements. Moreover, two-sided printed devices confine the functionalization or deposition of compounds for the detection of the analyte to smaller volume and closer to the surface of the device, improving the limits of detection. This is due to the fact that all three substrate materials are highly scattering (rough surfaces)—having the analyte and functionalization of the substrates closer to the surface or confined to a smaller volume minimized the loss of signal to scattering. Printing wax on both surfaces of the substrate with heat treatment to cause the wax to wick into the substrate fully confines the resulting device.

Since the read-out technique involves advanced image collection and process, it follows that a more homogeneous fluorescence signal on the detection element would lead to better performance of the device. Chemical functionalization of the paper or non-paper-based substrate on the detection element can improve quantification of the analytes such that coffee ring effect is minimized when the solvents used to carry the different reagents or chemicals dry. To eliminate or reduce coffee ring effect at the tracer detection stage, the uniform reagent such as lanthanide ions coating at the surface to detect analytes improves the homogeneity of the resulting fluorescence signal. Functionalized surface exhibiting high binding affinity to lanthanide ions enables even distribution of lanthanide ions on the detection element surface, which then facilitates homogenous fluorescence signal after detecting tracers.

To demonstrate chemical functionalization, a cyclen-derivative was used as a ligand for Ln(III) complexes functionalized on the detection element since its tetra-aza cycle forms very stable lanthanide chelates, and it is amenable to synthetic elaboration for structural versatility. A schematic description of the cyclen derivatization is shown in FIG. 10A. Tris-tert-butyl ester of cyclen (DO3A-tBu) was synthesized followed by reaction with 3-iodopropyltrimethoxysilane to afford, DO3A-tBu with a pendant trimethoxysilyl group (DO3A-tBu-TMS), that allows for organosilanization with surface hydroxyl groups of a substrate. In FIG. 10B shows creating a functional substrate coated with the cyclen derivatives. To do so, plasma-treated substrate, quartz in this particular experiment, was soaked in a toluene solution of DO3A-tBu-TMS for 24 h followed by washing with pure toluene, which is referred to as Q-DO3A-tBu. Then, the substrate was treated with trifluoroacetic acid to convert tris-tert-butyl ester of DO3A-tBu to carboxylic acids to give Q-DO3A. Lastly, lanthanide complexes of Q-DO3A-Ln$^+$ were prepared by soaking the functionalized substrate into a lanthanide ion solution for 1 h.

Figure 11E:
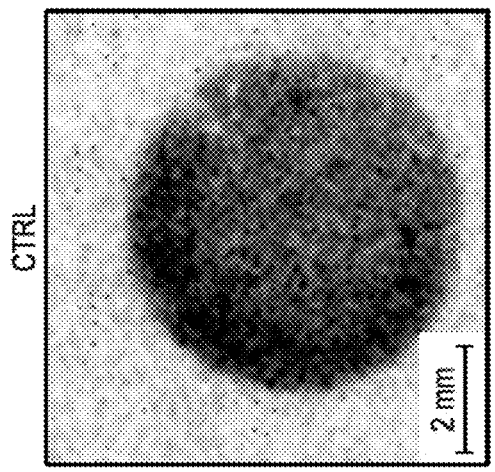
FIGS. 11A-11F show results of optical detection of DPA using quartz-based substrates functionalized with the cyclen-derivative and their negative control experiments deposited with DI water containing no DPA.
Figure 11F:
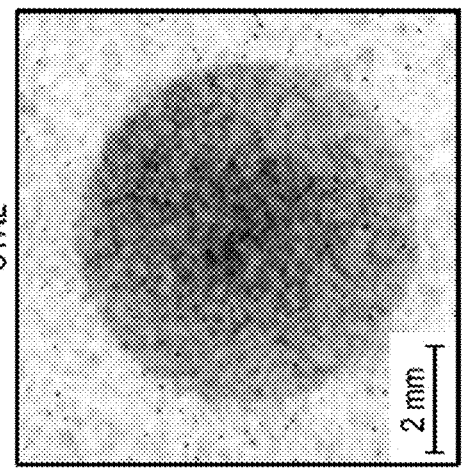
Figure 11C:
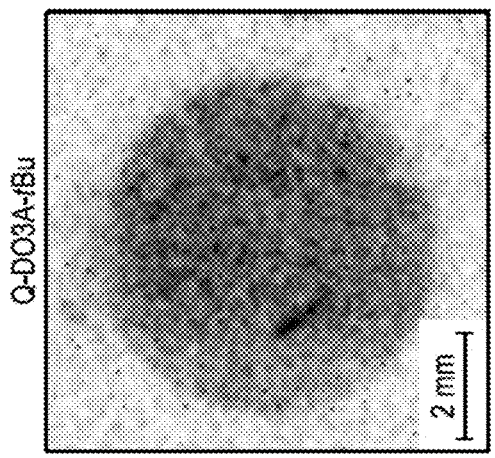
Figure 11D:
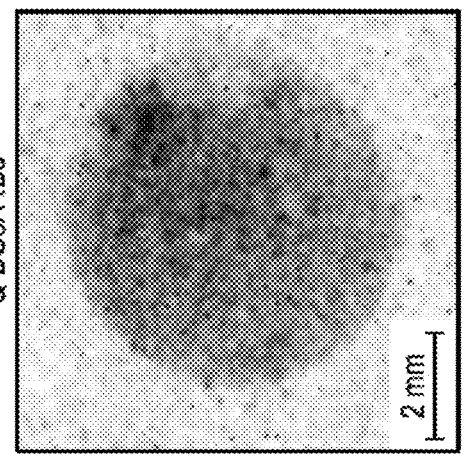
Figure 11A:
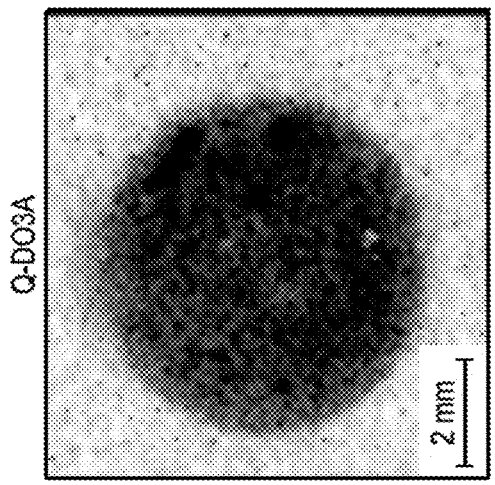
Figure 11B:
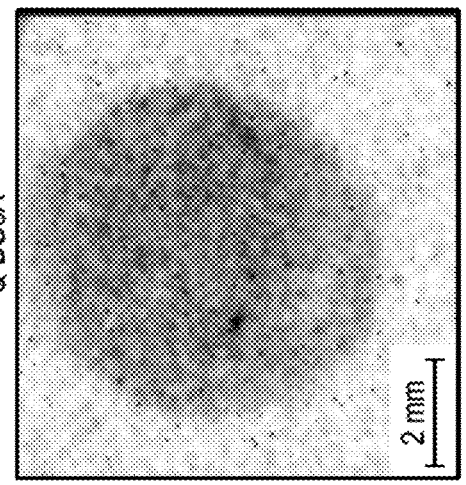

To investigate the effect of functionalized surface on uniformity of the resultant fluorescence signal over the detectoin area, quartz-fiber based subsrtates were functionalized as described above with 1E-5 M of terbium chloride in 1 M sodium acetate buffer solution. A control sample was prepared by soaking a non-functionalized quartz substrate into 1E-5 M of terbium chloride in 1 M sodium acetate buffer solution for 1 h. Then, 10 μL of 10 ppm DPA tracer solution was dropped onto each substrate. The fluorescence detection was carried out using a Teledyne Princeton Instruments PI-Max 4 emICCD time-resolved fluorescence camera with pulsed LED excitation at 265 nm (Thorlabs). The results are shown in FIGS. 11A-11F. In particular, FIGS. 11A, 11C and 11E show optical detection of DPA using quartz-based substrates functionalized with the cyclen-drivative. FIGS. 11B, 11D and 11F show corresponding negative control experiments deposited with DI water containing no DPA.

It was found that the Q-DO3A-Tb$^+$ elicited an improved fluorescence uniformity by forming complexes with DPA compared to the control sample, which suggests that the surface functionalization minimized the coffee-ring effect (FIG. 11E). A relatively weak but discernible fluorescence signal in the control sample may result from the residual terbium ions remain in fibrous quartz substrate while soaking in the terbium solution, which can create fluorescent complexes with DPA. However, uneven fluorescence pattern was observed due to the irregularly distributed (non-surface-bound) terbium ions while solvent evaporation (FIG. 11A). The Q-DO3A-tBu soaked into a terbium solution did not give any measurably fluorescence after drop-casting 10 μL of 10 ppm DPA tracer solution (FIG. 11C), which is likely due to either the incompatibility of the highly hydrophobic substrate surface with the aqueous solutions or relatively weak binding affinity of DO3A-tBu to terbium ions compared to that of DO3A having additional chelating groups, carboxylic acid moieties. The results for negative control experiments in which each substrate was deposited with 10 μL of DI water are shown in FIGS. 11B, 11D and 11F, indicating no appreciable differences among the three samples.

Figure 12A:
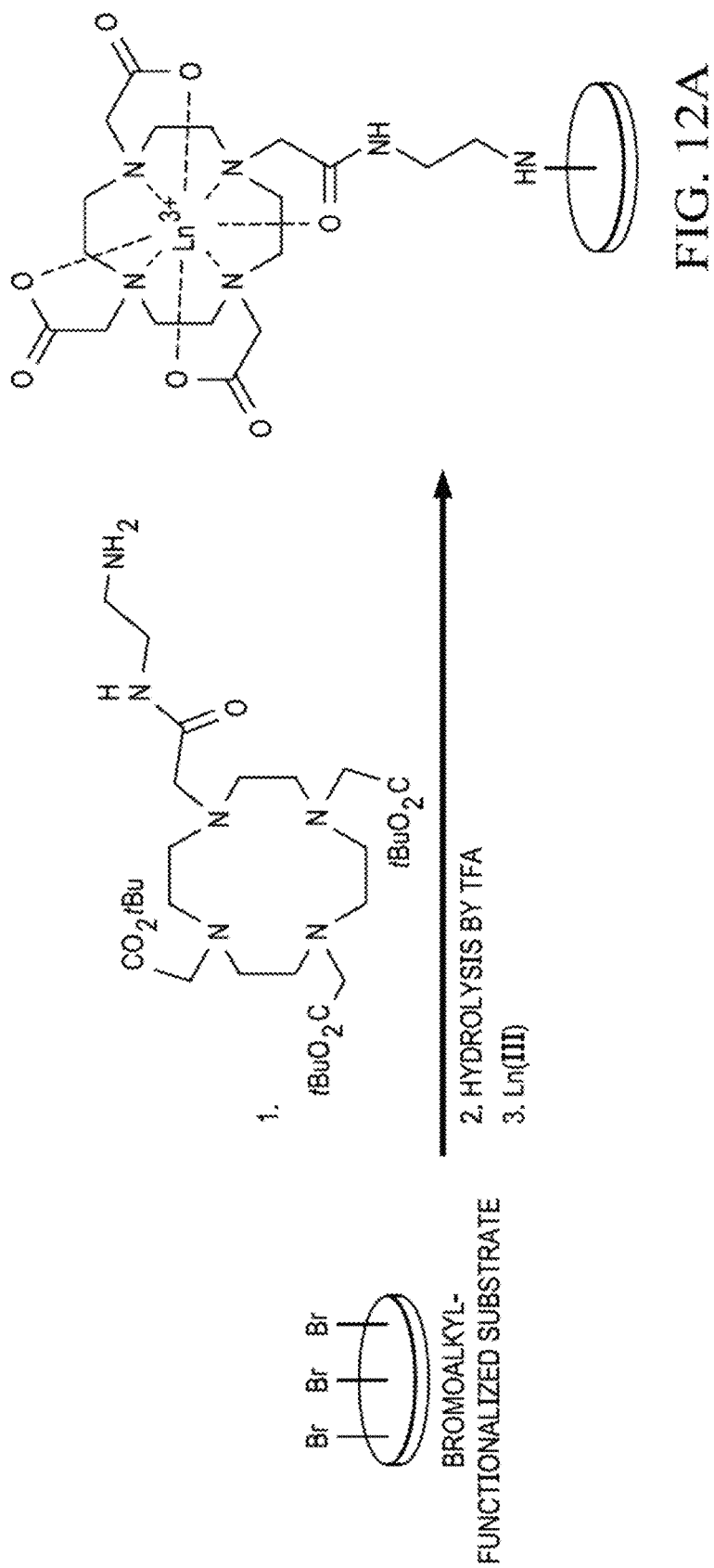
FIGS. 12A and 12B show strategies for surface functionalization on bromoalkyl-substrate and terminal alkyne-substrate, respectively, using cyclen-based ligands, respectively.
Figure 12B:
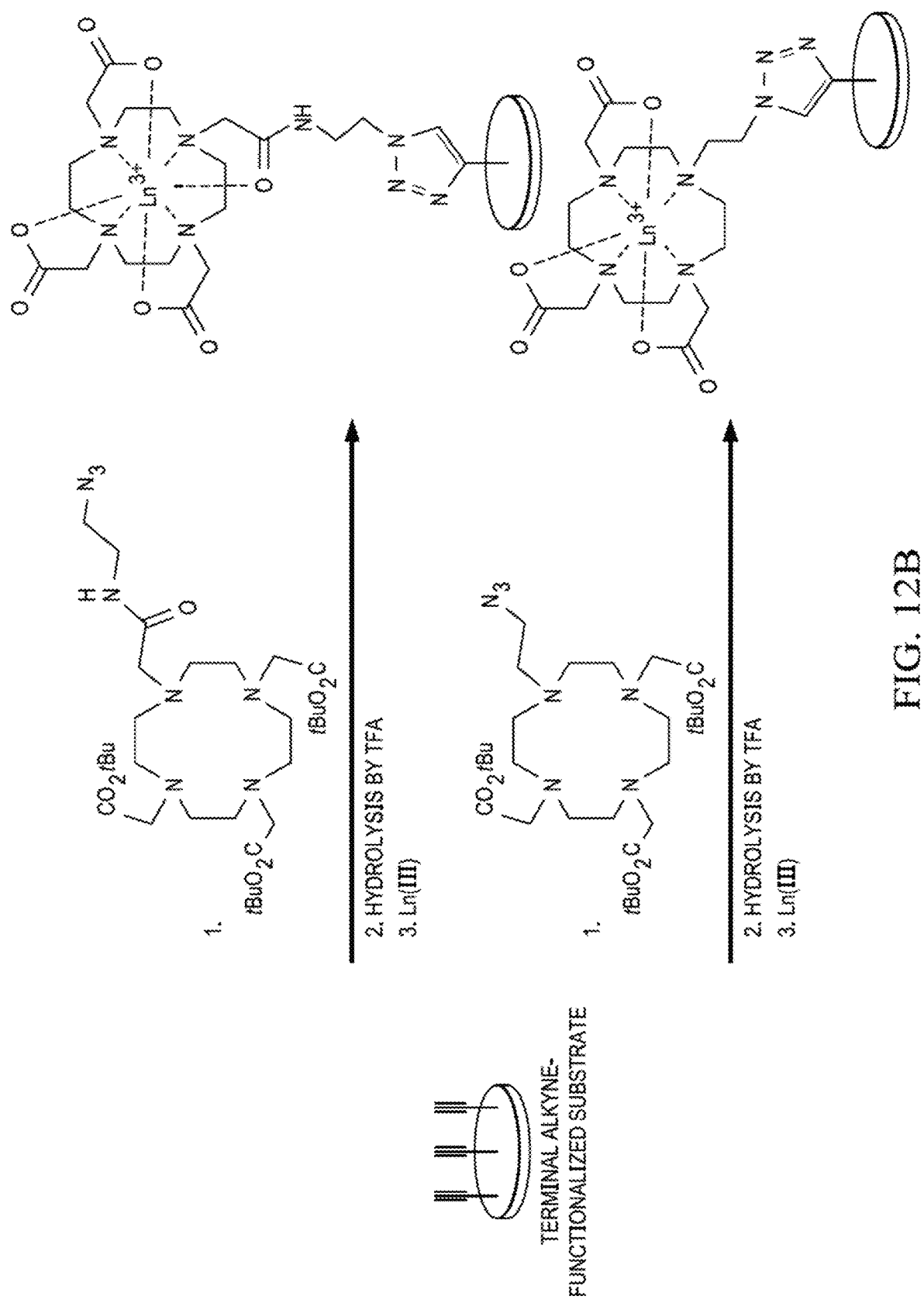

Some additional candidate substrates functionalized with cyclen-based ligands are also shown in FIGS. 12A and 12B. FIGS. 12A and 12B show strategies for surface functionalization on bromoalkyl-substrate and terminal alkyne-substrate, respectively, using cyclen-based ligands, respectively.

Figure 13A:
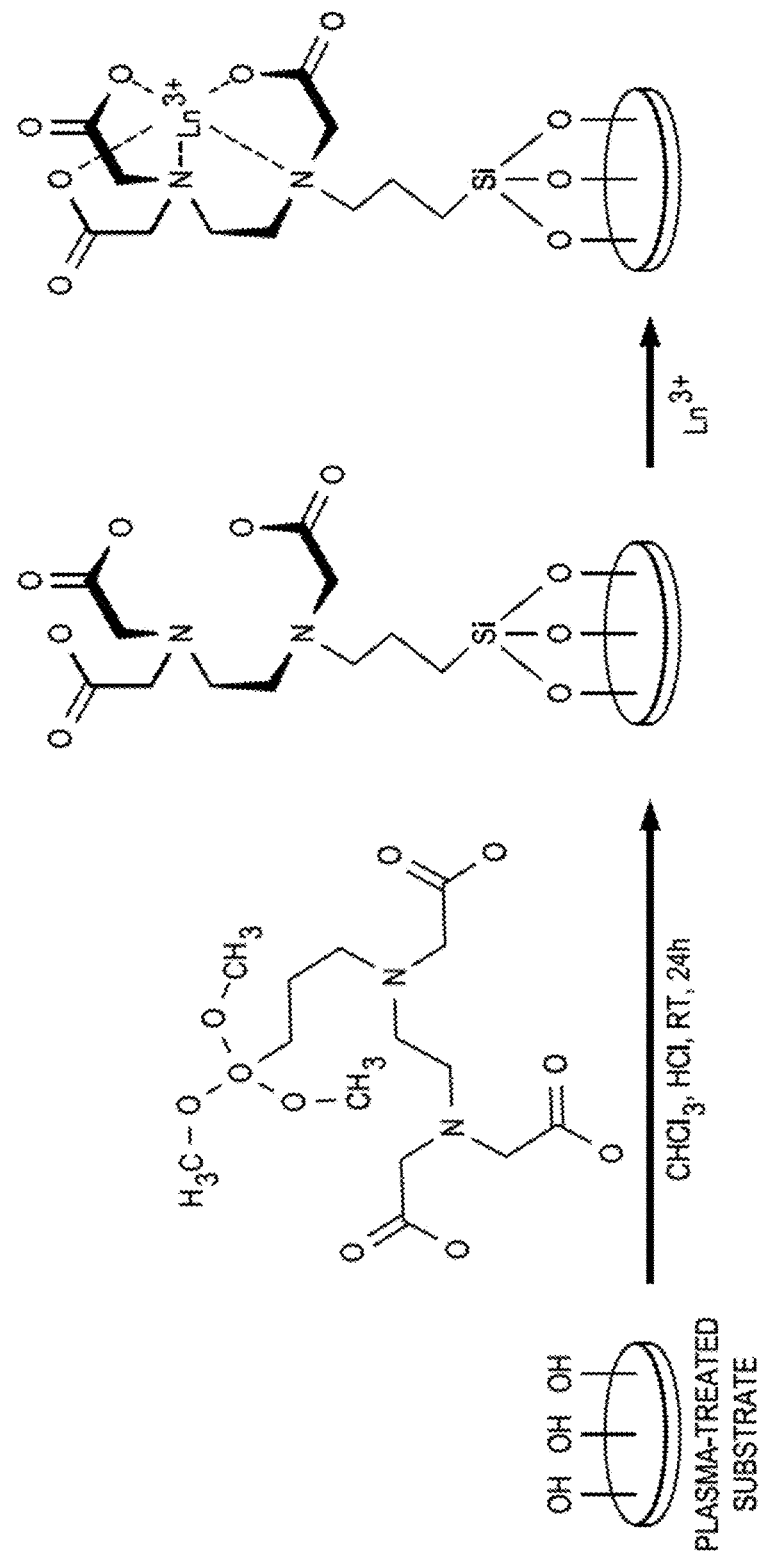
FIGS. 13A and 13B show schematic description of the surface functionalization with carboxylate and phosphate groups, respectively, via hydrolysis reaction of silane compounds.
Figure 13B:
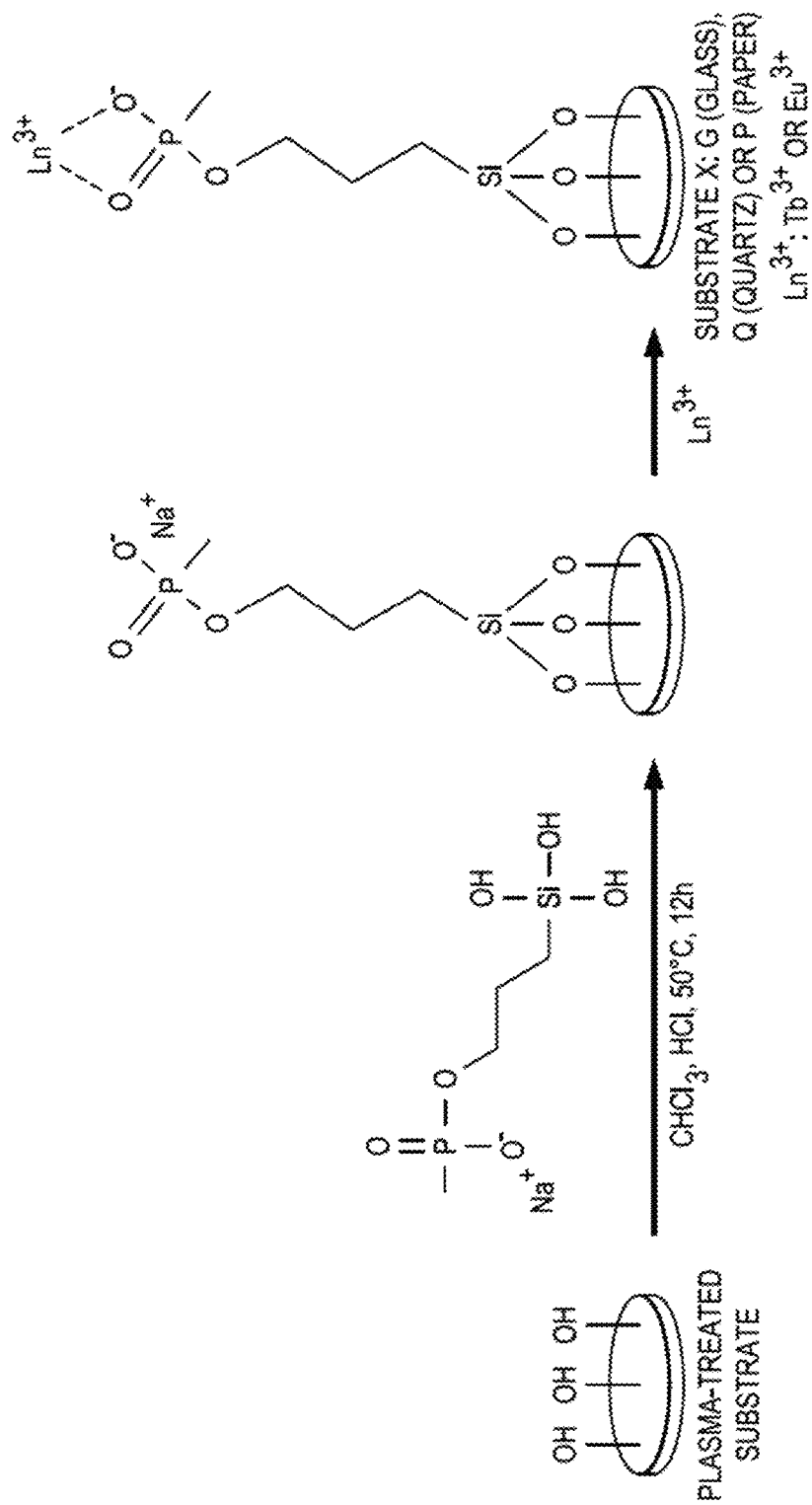

To demonstrate chemical functionalization, paper and quartz based surfaces can also be functionalized by other chelating agents to immobilize rare earth ions on their surfaces. For examples, polydentate ligand chelating agent EDTA or phosphonate compounds can be chemically grafted on various surfaces via silane chemistry, as schematically illustrated in FIGS. 13A and 13B. To generate enough surface hydroxyl groups for effective coating, the surface of paper was first treated by oxygen plasma and the surface of quartz was treated by Piranha solution (3:1 in volume ratio of concentrated $H_2SO_4$ and 30% $H_2O_2$ solution). Silane coupling agents, (trimethoxysilylpropyl)ethylenediaminetriacetate and 3-(trihydroxysilyl)propyl methylphosphonate have been used for the surface functionalization through hydrolysis reaction in existence of acid (HCl) or base ($NH_3 \cdot H_2O$) as catalyst. Trivalent europium and terbium ions have been known to complex with ligands, typically through 9 coordination sites. These grafted ligands on the surface could partially coordinate with $Ln^{3+}$, and thus the $Ln^{3+}$ ions can be immobilized on surface homogeneously while still retaining some coordination sites for the analytes of interest, such as DPA or BSPPDA. The ligand-$Ln^{3+}$ complexes also minimize water molecules binding to the $Ln^{3+}$ because it is known that water binding may quench the fluorescence emission of $Ln^{3+}$ in some extent.

Further, in the case of the lanthanide ions used for the detection of dipicolinic acid based or BSPPDA-based tracers, chemical functionalization of the substrate on the detection element could prevent hydroxyl quenching of the lanthanide ions, leading to better signal stability and a more robust read-out.

Disclosed above are methods and devices for detecting analytes down to trace/ultra-trace levels (ppb and below) using optical methods. The inherent fluorescence of paper substrates is a major limitation. Use of a low background substrate (such as quartz), combined with methods of fabricating the device on this substrate, and use of a time-resolved fluorescence read-out technique lowers the background fluorescence signal.

Using the specific wax additives and heat treatment processing parameters to obtain the hydrophobic barrier are advantageous, as is the use of a time-resolved fluorescence camera as a read-out instrument for time-gated signal to reduce background signal.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

In one embodiment, the device could be used for the detection of fluorescent analytes in reservoir fluids. Sensitivity of detection is enhanced by the device because interferents, such as polycyclic aromatic hydrocarbons and divalent ions, in the fluid are removed when it wicked through the separation element 105. By manipulating the pH of the reservoir fluids, specific functionalization of element 105 with (C8, C18, ion-exchanging or desalting resin) can be used to entrap and separate the interfering species (or both) chromatographically with the selectivity as determined by the affinity of the chemical species in the fluid and the surface functionalization of the substrate. The fluorescent analyte of interest can thus elute to the detection element 115 and quantified without background signal from other undesired fluorescent species.

What is claimed is:

1. A device for chemical analysis of a fluid sample, the device comprising:
   a first separation element formed on a substrate for receiving the fluid sample, the first separation element comprising a hydrophilic channel with a hydrophobic border that separates water from hydrocarbons in the fluid sample, the hydrophobic border at least partially surrounding the first separation element;
   a plurality of second separation elements fluidically connected to the first separation element and formed on the substrate, each second separation element comprising a wicking channel with a different functionalized surface configured to react with and separate a different component from the fluid sample such that each second separation element reacts with and separates different components from the fluid sample; and
   a different detection element fluidically connected to each second separation element and formed on the substrate, each detection element having a surface comprising one or more lanthanide ions that emit a fluorescence signal upon binding with one or more analytes present in the fluid sample, each emitted fluorescence signal indicative of a different analyte and capable of being optically detected by a detector.

2. The device of claim 1, wherein the substrate is quartz.

3. The device of claim 1, wherein the first separation element comprises a hydrophobic surface formed by printing ink having wax additives on the substrate followed by heat treatment.

4. The device of claim 3, wherein the printing ink has from about 15 wt % up to about 50 wt % of wax additives.

5. The device of claim 3, wherein the wax additive is up to 50 wt % of sunflower wax additive.

6. The device of claim 1, wherein the one or more analytes comprises dipicolinic acid.

7. The device of claim 1, wherein at least one of the functionalized surfaces comprises a hydrophobic material comprising C18, C8, fluorinated silanes, or fluoropolymers.

8. The device of claim 1, wherein a first detection element of the detection elements contains europium ions, and a second detection element of the detection elements contains terbium ions.

9. The device of claim 1, wherein the hydrophilic channel with the hydrophobic border causes hydrocarbons of the fluid sample to remain within the hydrophobic border.

10. The device of claim 1, wherein the plurality of second separation elements are configured to perform a finer separation of the fluid sample than the first separation element.

11. The device of claim 1, wherein the substrate is quartz, and the device is configured to detect tracer concentrations of 10 ppb.

12. The device of claim 1, wherein the device is configured to detect multiple analytes in the fluid sample simultaneously.

13. The device of claim 1, wherein the device is double-sided and each detection element is fully confined on the substrate.

14. The device of claim 1, wherein at least one of the different functionalized surfaces is coated with a cyclen derivative.

15. A system for chemical analysis, the system comprising:
- a fluid sample comprising a hydrocarbon and one or more interferents;
- a device comprising:
  - a first separation element formed on a substrate, the first separation element configured to separate the hydrocarbon from the fluid sample;
  - a plurality of second separation elements fluidically connected to the first separation element and formed on the substrate, each second separation element configured to separate a different interferent of the one or more interferents from the fluid sample; and
  - a different detection element fluidically connected to each second separation element and formed on the substrate, a first detection element of the different detection elements comprising europium ions that emit a first fluorescence signal upon binding with one or more analytes in the fluid sample, and a second detection element of the different detection elements comprising terbium ions that emit a second fluorescence signal upon binding with one or more analytes in the fluid sample;
- a fluorescence camera configured to detect the first fluorescence signal and the second fluorescence signal; and
- a processor configured to detect a presence of an acid in the fluid sample based on the detection of the first fluorescence signal and the second fluorescence signal.

16. The system of claim 15, wherein the fluorescence camera is a time-resolved fluorescence camera.

17. The system of claim 15, wherein the substrate is quartz.

18. The system of claim 15, wherein the first separation element is configured such that the hydrocarbon in the fluid sample wets a material of the first separation element and remains in the first separation element.

19. The system of claim 18, wherein the fluid sample further comprises water, and the first separation element is configured such that the water in the fluid sample beads up due to a hydrophobicity of the material of the first separation element.

20. The system of claim 19, wherein the device is configured such that the water in the fluid sample contacts a hydrophilic channel with a hydrophobic border of the first separation element and moves down a respective wicking channel of each second separation element of the plurality of second separation elements, driven by capillary action.

21. The system of claim 20, wherein each second separation element comprises a different chemically functionalized surface that traps the one or more interferents from the fluid sample as the fluid sample moves down each wicking channel.

22. The system of claim 21, wherein each chemically functionalized surface comprises a different hydrophobic material selected from the group consisting of C18, C8, fluorinated silanes, and fluoropolymers.

23. The system of claim 15, further comprising a wellsite that produces the fluid sample.

24. The system of claim 15, wherein the fluid sample is disposed in the first separation element.

* * * * *